United States Patent
Oh et al.

(10) Patent No.: US 7,659,388 B2
(45) Date of Patent: Feb. 9, 2010

(54) METHOD AND COMPOSITIONS FOR DETECTING RESPIRATORY DISEASE-CAUSING BACTERIAL SPECIES

(75) Inventors: Ji-young Oh, Suwon-si (KR); Sang-hyun Paek, Seoul (KR); Kyung-hee Park, Seoul (KR); Jung-nam Lee, Incheon (KR); Jong-suk Chung, Suwon-si (KR); Ah-gi Kim, Yongin-si (KR)

(73) Assignee: Samsung Electronics Co., Ltd. (KR)

( * ) Notice: Subject to any disclaimer, the term of this patent is extended or adjusted under 35 U.S.C. 154(b) by 68 days.

(21) Appl. No.: 11/862,758

(22) Filed: Sep. 27, 2007

(65) Prior Publication Data

US 2008/0081770 A1    Apr. 3, 2008

(30) Foreign Application Priority Data

Sep. 28, 2006    (KR) .................. 10-2006-0094673

(51) Int. Cl.
*C07H 21/02* (2006.01)
*C07H 21/04* (2006.01)
*C12Q 1/68* (2006.01)

(52) U.S. Cl. .................. 536/24.3; 435/6; 536/23.1; 536/24.33

(58) Field of Classification Search .................. None
See application file for complete search history.

(56) References Cited

U.S. PATENT DOCUMENTS

| | | | |
|---|---|---|---|
| 4,851,330 A | 7/1989 | Kohne | |
| 5,288,611 A | 2/1994 | Kohne | |
| 5,525,718 A | 6/1996 | Ohasi et al. | |
| 5,830,654 A | 11/1998 | Milliman | |
| 6,001,564 A | 12/1999 | Bergeron et al. | |

FOREIGN PATENT DOCUMENTS

KR    1020060073454 A    6/2006

OTHER PUBLICATIONS

Chizhikov et al., "Microarray Analysis of Microbial Virulence Factors," Applied and Environmental Microbiology, Jul. 2001, vol. 67, No. 7, pp. 3258-3263.*
GenBank Accession No. 88758847, available Feb. 2008.*
GenBank Accession No. 35187096, available Apr. 2004.*
GenBank Accession No. 509757, available Nov. 2006 (first available 1993).*
GenBank Accession No. 2961259, available Apr. 2005.*
GenBank Accession No. 43279, available Apr. 2005.*
GenBank Accession No. 40095415, available Dec. 2003.*
GenBank Accession No. 82941249, available Dec. 2005.*
GenBank Accession No. 1800308, available Jan. 1997.*
GenBank Accession No. 14135055, available May 2001.*
GenBank Accession No. 162911477, available Dec. 2007 (first available Mar. 2006).*
GenBank Accession No. 4928269, available Jun. 1999.*
GenBank Accession No. 4928267, available Jun. 1999.*
GenBank Accession No. 44810, available Feb. 1999.*
NCBI GenBank Accession No. CT025812.2, dated Feb. 24, 2006.
NCBI GenBank Accession No. U16754.1, dated Sep. 12, 1995.
NCBI GenBank Accession No. M64064.1, dated Apr. 26, 1993.
NCBI GenBank Accession No. Z26655.1, dated Jul. 1, 1994.
NCBI GenBank Accession No. Y13230.1, dated Apr. 18, 2005.
NCBI GenBank Accession No. X67639.1, dated Apr. 18, 2005.
NCBI GenBank Accession No. AY823268.1, dated Jun. 11, 2005.
NCBI GenBank Accession No. AF095215.1, dated May 1, 2002.
NCBI GenBank Accession No. L12346.1, dated Jul. 26, 1993.
NCBI GenBank Accession No. AB02461.1, dated Aug. 31, 1999.
NCBI GenBank Accession No. K01397.1, dated Feb. 11, 2002.
NCBI GenBank Accession No. M13812.1, dated Apr. 26, 1993.
Santalucia, J.; "A unified view of polymer, dumbbell, and oligonucleotide DNA nearest-neighbor thermodynaimcs"; Proc. Natl. Acad. Sci. USA; vol. 95; pp. 1460-1465; Feb. 1998.

* cited by examiner

*Primary Examiner*—Young J Kim
(74) *Attorney, Agent, or Firm*—Cantor Colburn LLP

(57) ABSTRACT

Provided are a primer set for specifically amplifying target sequence(s) of twelve respiratory disease-causing bacterial species, a probe set specifically hybridizing with target sequence(s) of twelve respiratory disease-causing bacterial species, a microarray comprising the probe set, and a method of detecting a respiratory disease-causing bacterial species using the probe set.

2 Claims, 5 Drawing Sheets

FIG. 1B

|  |  | Column | | | | | | | | | | | | |
|---|---|---|---|---|---|---|---|---|---|---|---|---|---|---|
|  |  | 0 | 1 | 2 | 3 | 4 | 5 | 6 | 7 | 8 | 9 | 10 | 11 | 12 |
| Row | 1 |  |  |  |  |  |  | – |  | 32 | 33 |  |  | – |
|  | 2 |  |  |  |  | 46 | 45 | – |  |  | 56 | 58 | 57 | – |
|  | 3 |  |  |  |  |  |  | 49 | 29 | 30 | 28 |  | 31 |  |
|  | 4 |  |  |  | 48 | 47 | – | – | 40 | 41 | 42 | 25 | 26 | 27 |
|  | 5 |  |  |  | 52 | 53 | 54 | 55 | 34 | 35 |  | 39 |  |  |
|  | 6 |  |  | 50 | 51 | – | – | – |  |  |  |  |  |  |

SEQUENCE LISTING

```
<160> NUMBER OF SEQ ID NOS: 74

<210> SEQ ID NO 1
<211> LENGTH: 22
<212> TYPE: DNA
<213> ORGANISM: Artificial Sequence
<220> FEATURE:
<223> OTHER INFORMATION: primer : forward

<400> SEQUENCE: 1
caggtgaata ttagtgcgac tt                                              22

<210> SEQ ID NO 2
<211> LENGTH: 23
<212> TYPE: DNA
<213> ORGANISM: Artificial Sequence
<220> FEATURE:
<223> OTHER INFORMATION: primer :reverse

<400> SEQUENCE: 2
ttgttgtcgc actatagtag agt                                             23

<210> SEQ ID NO 3
<211> LENGTH: 21
<212> TYPE: DNA
<213> ORGANISM: Artificial Sequence
<220> FEATURE:
<223> OTHER INFORMATION: primer : forward

<400> SEQUENCE: 3
ggtgcgtgtg tttcgtgcgt g                                               21

<210> SEQ ID NO 4
<211> LENGTH: 21
<212> TYPE: DNA
<213> ORGANISM: Artificial Sequence
<220> FEATURE:
<223> OTHER INFORMATION: primer : reverse

<400> SEQUENCE: 4
```
ttaagcgccc atgccgaggg a                                          21

<210> SEQ ID NO 5
<211> LENGTH: 22
<212> TYPE: DNA
<213> ORGANISM: Artificial Sequence
<220> FEATURE:
<223> OTHER INFORMATION: primer : forward

<400> SEQUENCE: 5
aggagcttct aatggttaca tt                                         22

<210> SEQ ID NO 6
<211> LENGTH: 22
<212> TYPE: DNA
<213> ORGANISM: Artificial Sequence
<220> FEATURE:
<223> OTHER INFORMATION: primer: reverse

<400> SEQUENCE: 6
gactgtgcat attggaattc ag                                         22

<210> SEQ ID NO 7
<211> LENGTH: 23
<212> TYPE: DNA
<213> ORGANISM: Artificial Sequence
<220> FEATURE:
<223> OTHER INFORMATION: primer: forward

<400> SEQUENCE: 7
ttatcgctcc ccacatctca cct                                        23

<210> SEQ ID NO 8
<211> LENGTH: 21
<212> TYPE: DNA
<213> ORGANISM: Artificial Sequence
<220> FEATURE:
<223> OTHER INFORMATION: primer: reverse

<400> SEQUENCE: 8
atcgccgcga ttcgactact g                                          21

<210> SEQ ID NO 9
<211> LENGTH: 22
<212> TYPE: DNA
<213> ORGANISM: Artificial Sequence
<220> FEATURE:
<223> OTHER INFORMATION: primer : forward

<400> SEQUENCE: 9
gcaggacgat gacatgaaac ag                                         22

<210> SEQ ID NO 10
<211> LENGTH: 22
<212> TYPE: DNA
<213> ORGANISM: Artificial Sequence
<220> FEATURE:
<223> OTHER INFORMATION: primer : reverse

<400> SEQUENCE: 10
taatctcacg accgacgtct tc                                         22

<210> SEQ ID NO 11
<211> LENGTH: 23
<212> TYPE: DNA

-continued

```
<213> ORGANISM: Artificial Sequence
<220> FEATURE:
<223> OTHER INFORMATION: primer : forward

<400> SEQUENCE: 11
tcgtaaacac cttatctggc cta                                              23

<210> SEQ ID NO 12
<211> LENGTH: 23
<212> TYPE: DNA
<213> ORGANISM: Artificial Sequence
<220> FEATURE:
<223> OTHER INFORMATION: primer : reverse

<400> SEQUENCE: 12
tgcggtgaat agattaatac act                                              23

<210> SEQ ID NO 13
<211> LENGTH: 21
<212> TYPE: DNA
<213> ORGANISM: Artificial Sequence
<220> FEATURE:
<223> OTHER INFORMATION: primer : forward

<400> SEQUENCE: 13
cgacagcagt catctgcaac t                                                21

<210> SEQ ID NO 14
<211> LENGTH: 23
<212> TYPE: DNA
<213> ORGANISM: Artificial Sequence
<220> FEATURE:
<223> OTHER INFORMATION: primer: reverse

<400> SEQUENCE: 14
gcaggtgtga gtcttcatac atc                                              23

<210> SEQ ID NO 15
<211> LENGTH: 21
<212> TYPE: DNA
<213> ORGANISM: Artificial Sequence
<220> FEATURE:
<223> OTHER INFORMATION: primer: forward

<400> SEQUENCE: 15
tatagcattg gtgccgattt g                                                21

<210> SEQ ID NO 16
<211> LENGTH: 21
<212> TYPE: DNA
<213> ORGANISM: Artificial Sequence
<220> FEATURE:
<223> OTHER INFORMATION: primer : reverse

<400> SEQUENCE: 16
actgtcaaaa acggtaccat c                                                21

<210> SEQ ID NO 17
<211> LENGTH: 21
<212> TYPE: DNA
<213> ORGANISM: Artificial Sequence
<220> FEATURE:
<223> OTHER INFORMATION: primer: forward

<400> SEQUENCE: 17
aaccactgct tttgcagctg t                                                21
```

<210> SEQ ID NO 18
<211> LENGTH: 21
<212> TYPE: DNA
<213> ORGANISM: Artificial Sequence
<220> FEATURE:
<223> OTHER INFORMATION: primer: reverse

<400> SEQUENCE: 18
gcattatgac ccatgccacg a                                              21

<210> SEQ ID NO 19
<211> LENGTH: 21
<212> TYPE: DNA
<213> ORGANISM: Artificial Sequence
<220> FEATURE:
<223> OTHER INFORMATION: primer: forward

<400> SEQUENCE: 19
cacgagtgac ggaaacacct c                                              21

<210> SEQ ID NO 20
<211> LENGTH: 22
<212> TYPE: DNA
<213> ORGANISM: Artificial Sequence
<220> FEATURE:
<223> OTHER INFORMATION: primer : reverse

<400> SEQUENCE: 20
ttaaagaact ctaagcggag ac                                             22

<210> SEQ ID NO 21
<211> LENGTH: 24
<212> TYPE: DNA
<213> ORGANISM: Artificial Sequence
<220> FEATURE:
<223> OTHER INFORMATION: primer : forward

<400> SEQUENCE: 21
gacaacgccc tcagcatcac cagc                                           24

<210> SEQ ID NO 22
<211> LENGTH: 24
<212> TYPE: DNA
<213> ORGANISM: Artificial Sequence
<220> FEATURE:
<223> OTHER INFORMATION: primer : reverse

<400> SEQUENCE: 22
cgctggccca ttcgctccag cgct                                           24

<210> SEQ ID NO 23
<211> LENGTH: 21
<212> TYPE: DNA
<213> ORGANISM: Artificial Sequence
<220> FEATURE:
<223> OTHER INFORMATION: primer : forward

<400> SEQUENCE: 23
acagtgtcaa aatagtgcgt t                                              21

<210> SEQ ID NO 24
<211> LENGTH: 21
<212> TYPE: DNA
<213> ORGANISM: Artificial Sequence
<220> FEATURE:

```
<223> OTHER INFORMATION: primer : reverse

<400> SEQUENCE: 24
agttgagtgt gcgtgtactt g                                              21

<210> SEQ ID NO 25
<211> LENGTH: 23
<212> TYPE: DNA
<213> ORGANISM: Artificial Sequence
<220> FEATURE:
<223> OTHER INFORMATION: probe

<400> SEQUENCE: 25
ccattaacga tagcgttgta acc                                            23

<210> SEQ ID NO 26
<211> LENGTH: 21
<212> TYPE: DNA
<213> ORGANISM: Artificial Sequence
<220> FEATURE:
<223> OTHER INFORMATION: probe

<400> SEQUENCE: 26
gagcgcgaat tatcgggtgt a                                              21

<210> SEQ ID NO 27
<211> LENGTH: 21
<212> TYPE: DNA
<213> ORGANISM: Artificial Sequence
<220> FEATURE:
<223> OTHER INFORMATION: probe

<400> SEQUENCE: 27
gcgcgaatta tcgggtgtaa a                                              21

<210> SEQ ID NO 28
<211> LENGTH: 23
<212> TYPE: DNA
<213> ORGANISM: Artificial Sequence
<220> FEATURE:
<223> OTHER INFORMATION: probe

<400> SEQUENCE: 28
tttcctttgt attggttcgc agc                                            23

<210> SEQ ID NO 29
<211> LENGTH: 22
<212> TYPE: DNA
<213> ORGANISM: Artificial Sequence
<220> FEATURE:
<223> OTHER INFORMATION: probe

<400> SEQUENCE: 29
ctttgtattg gttcgcagct tc                                             22

<210> SEQ ID NO 30
<211> LENGTH: 22
<212> TYPE: DNA
<213> ORGANISM: Artificial Sequence
<220> FEATURE:
<223> OTHER INFORMATION: probe

<400> SEQUENCE: 30
gcgagtgcaa cgggaaataa ag                                             22
```

```
<210> SEQ ID NO 31
<211> LENGTH: 23
<212> TYPE: DNA
<213> ORGANISM: Artificial Sequence
<220> FEATURE:
<223> OTHER INFORMATION: probe

<400> SEQUENCE: 31
gcggttctcc acattgattc agg                                              23

<210> SEQ ID NO 32
<211> LENGTH: 23
<212> TYPE: DNA
<213> ORGANISM: Artificial Sequence
<220> FEATURE:
<223> OTHER INFORMATION: probe

<400> SEQUENCE: 32
ttgggatcgc tttgatgttt tct                                              23

<210> SEQ ID NO 33
<211> LENGTH: 23
<212> TYPE: DNA
<213> ORGANISM: Artificial Sequence
<220> FEATURE:
<223> OTHER INFORMATION: probe

<400> SEQUENCE: 33
acctctttct cttggagcgt agg                                              23

<210> SEQ ID NO 34
<211> LENGTH: 21
<212> TYPE: DNA
<213> ORGANISM: Artificial Sequence
<220> FEATURE:
<223> OTHER INFORMATION: probe

<400> SEQUENCE: 34
atcgccagca tttttcctg a                                                 21

<210> SEQ ID NO 35
<211> LENGTH: 21
<212> TYPE: DNA
<213> ORGANISM: Artificial Sequence
<220> FEATURE:
<223> OTHER INFORMATION: probe

<400> SEQUENCE: 35
ctgagctgac tccaacgact g                                                21

<210> SEQ ID NO 36
<211> LENGTH: 19
<212> TYPE: DNA
<213> ORGANISM: Artificial Sequence
<220> FEATURE:
<223> OTHER INFORMATION: probe

<400> SEQUENCE: 36
actggggtat gaagctgcg                                                   19

<210> SEQ ID NO 37
<211> LENGTH: 20
<212> TYPE: DNA
<213> ORGANISM: Artificial Sequence
<220> FEATURE:
<223> OTHER INFORMATION: probe
```

-continued

```
<400> SEQUENCE: 37
gtttcggttt gctggggtat                                               20

<210> SEQ ID NO 38
<211> LENGTH: 20
<212> TYPE: DNA
<213> ORGANISM: Artificial Sequence
<220> FEATURE:
<223> OTHER INFORMATION: probe

<400> SEQUENCE: 38
gtttcggttt actggggtat                                               20

<210> SEQ ID NO 39
<211> LENGTH: 21
<212> TYPE: DNA
<213> ORGANISM: Artificial Sequence
<220> FEATURE:
<223> OTHER INFORMATION: probe

<400> SEQUENCE: 39
cacgtcgttt cggtttactg g                                             21

<210> SEQ ID NO 40
<211> LENGTH: 22
<212> TYPE: DNA
<213> ORGANISM: Artificial Sequence
<220> FEATURE:
<223> OTHER INFORMATION: probe

<400> SEQUENCE: 40
taacaccatc atattttcca tc                                            22

<210> SEQ ID NO 41
<211> LENGTH: 22
<212> TYPE: DNA
<213> ORGANISM: Artificial Sequence
<220> FEATURE:
<223> OTHER INFORMATION: probe

<400> SEQUENCE: 41
ccatcatatt ttccatcatt ag                                            22

<210> SEQ ID NO 42
<211> LENGTH: 23
<212> TYPE: DNA
<213> ORGANISM: Artificial Sequence
<220> FEATURE:
<223> OTHER INFORMATION: probe

<400> SEQUENCE: 42
agtgtgatca tctggttatt ttc                                           23

<210> SEQ ID NO 43
<211> LENGTH: 21
<212> TYPE: DNA
<213> ORGANISM: Artificial Sequence
<220> FEATURE:
<223> OTHER INFORMATION: probe

<400> SEQUENCE: 43
aatcaaaayc ccygccaata c                                             21

<210> SEQ ID NO 44
<211> LENGTH: 22
```

```
<212> TYPE: DNA
<213> ORGANISM: Artificial Sequence
<220> FEATURE:
<223> OTHER INFORMATION: probe

<400> SEQUENCE: 44
aatcaaaayc tccygccaat ac                                              22

<210> SEQ ID NO 45
<211> LENGTH: 22
<212> TYPE: DNA
<213> ORGANISM: Artificial Sequence
<220> FEATURE:
<223> OTHER INFORMATION: probe

<400> SEQUENCE: 45
gtaacccacg taaatggggg cg                                              22

<210> SEQ ID NO 46
<211> LENGTH: 23
<212> TYPE: DNA
<213> ORGANISM: Artificial Sequence
<220> FEATURE:
<223> OTHER INFORMATION: probe

<400> SEQUENCE: 46
aacgtattcc cggctgcgat ctc                                             23

<210> SEQ ID NO 47
<211> LENGTH: 23
<212> TYPE: DNA
<213> ORGANISM: Artificial Sequence
<220> FEATURE:
<223> OTHER INFORMATION: probe

<400> SEQUENCE: 47
tggctaaagg catgcaagac gct                                             23

<210> SEQ ID NO 48
<211> LENGTH: 23
<212> TYPE: DNA
<213> ORGANISM: Artificial Sequence
<220> FEATURE:
<223> OTHER INFORMATION: probe

<400> SEQUENCE: 48
aggcatgcaa gacgctatga gtg                                             23

<210> SEQ ID NO 49
<211> LENGTH: 21
<212> TYPE: DNA
<213> ORGANISM: Artificial Sequence
<220> FEATURE:
<223> OTHER INFORMATION: probe

<400> SEQUENCE: 49
cagtgatcgc caaggtgcaa a                                               21

<210> SEQ ID NO 50
<211> LENGTH: 23
<212> TYPE: DNA
<213> ORGANISM: Artificial Sequence
<220> FEATURE:
<223> OTHER INFORMATION: probe

<400> SEQUENCE: 50
```

| | |
|---|---|
| ggtgtatgac cagtacatac cgc | 23 |

<210> SEQ ID NO 51
<211> LENGTH: 23
<212> TYPE: DNA
<213> ORGANISM: Artificial Sequence
<220> FEATURE:
<223> OTHER INFORMATION: probe

<400> SEQUENCE: 51

| | |
|---|---|
| gtatgaccag tacataccgc tgt | 23 |

<210> SEQ ID NO 52
<211> LENGTH: 21
<212> TYPE: DNA
<213> ORGANISM: Artificial Sequence
<220> FEATURE:
<223> OTHER INFORMATION: probe

<400> SEQUENCE: 52

| | |
|---|---|
| tctcgatggt gtagatcggc g | 21 |

<210> SEQ ID NO 53
<211> LENGTH: 21
<212> TYPE: DNA
<213> ORGANISM: Artificial Sequence
<220> FEATURE:
<223> OTHER INFORMATION: probe

<400> SEQUENCE: 53

| | |
|---|---|
| atggtgtaga tcggcgacat g | 21 |

<210> SEQ ID NO 54
<211> LENGTH: 21
<212> TYPE: DNA
<213> ORGANISM: Artificial Sequence
<220> FEATURE:
<223> OTHER INFORMATION: probe

<400> SEQUENCE: 54

| | |
|---|---|
| tagatcggcg acatgtggct g | 21 |

<210> SEQ ID NO 55
<211> LENGTH: 21
<212> TYPE: DNA
<213> ORGANISM: Artificial Sequence
<220> FEATURE:
<223> OTHER INFORMATION: probe

<400> SEQUENCE: 55

| | |
|---|---|
| gatcggcgac atgtggctga g | 21 |

<210> SEQ ID NO 56
<211> LENGTH: 22
<212> TYPE: DNA
<213> ORGANISM: Artificial Sequence
<220> FEATURE:
<223> OTHER INFORMATION: probe

<400> SEQUENCE: 56

| | |
|---|---|
| tctacaagcc taatcgtgac ta | 22 |

<210> SEQ ID NO 57
<211> LENGTH: 22
<212> TYPE: DNA
<213> ORGANISM: Artificial Sequence

```
<220> FEATURE:
<223> OTHER INFORMATION: probe

<400> SEQUENCE: 57
ctatctacaa gcctaatcgt ga                                          22

<210> SEQ ID NO 58
<211> LENGTH: 23
<212> TYPE: DNA
<213> ORGANISM: Artificial Sequence
<220> FEATURE:
<223> OTHER INFORMATION: probe

<400> SEQUENCE: 58
agattgtctt ctttgtaagg tag                                         23

<210> SEQ ID NO 59
<211> LENGTH: 23
<212> TYPE: DNA
<213> ORGANISM: Artificial Sequence
<220> FEATURE:
<223> OTHER INFORMATION: probe

<400> SEQUENCE: 59
gcgtaccttt tgtataatgg gtc                                         23

<210> SEQ ID NO 60
<211> LENGTH: 19
<212> TYPE: DNA
<213> ORGANISM: Artificial Sequence
<220> FEATURE:
<223> OTHER INFORMATION: probe

<400> SEQUENCE: 60
cagaccgcca gctaaggtc                                              19

<210> SEQ ID NO 61
<211> LENGTH: 19
<212> TYPE: DNA
<213> ORGANISM: Artificial Sequence
<220> FEATURE:
<223> OTHER INFORMATION: probe

<400> SEQUENCE: 61
tgtcgggtaa gttccgacc                                              19

<210> SEQ ID NO 62
<211> LENGTH: 19
<212> TYPE: DNA
<213> ORGANISM: Artificial Sequence
<220> FEATURE:
<223> OTHER INFORMATION: probe

<400> SEQUENCE: 62
tagtgatccg gtggttcyg                                              19

<210> SEQ ID NO 63
<211> LENGTH: 3111
<212> TYPE: DNA
<213> ORGANISM: Acinetobacter baumannii
<220> FEATURE:
<221> NAME/KEY: misc_feature
<222> LOCATION: (1)..(3111)
<223> OTHER INFORMATION: Genbank accession Nos. AF370885, CT025812,
      CP000521 : AdeB gene

<400> SEQUENCE: 63
```

```
atgatgtcac aatttttat tcgtcgtccc gttttgctt gggttatygc gatcttcatt      60
attatatttg gattgctgag yattcctaaa ctgccaattg cacgttttcc aagtgtrgcc    120
ccgccacagg tgaatattag tgcgacttat cctggtgcta cagctaaaac cattaacgat   180
agcgttgtaa ccttaattga gcgcgaatta tcgggtgtaa aaaatctact ctactatagt   240
gcgacaacag atacctccgg tacagcagag attacsgcta cgtttaaacc rggcacagat   300
gtggaaatgg ctcaggtyga cgttcaaaat aaaatcaagg ctgtagaagc tcgcttrccg   360
caagtygtac gtcagcaagg yttacaggtt gargcttcat cgtccggatt tttaatgctg   420
gtcgggatta actctccaaa taatcaatat tccgaagttg atttgagtga ttatttggtt   480
cgaaatgttg tagaagagct aaaacgtgtc gaaggtgtag ggaaggttca atctttcggt   540
gcmgagaaag ctatgcgtat ttgggtcgac ccgaataagc ttgtttctta cggtttatcg   600
attagtgatg tgaataatgc cattcgtgaa aataatgtcg aaattgcacc cggccgactt   660
ggtgatttac cagctgaaaa aggccagctc attactattc cattgtctgc tcaagggcaa   720
ttgtctagtc tygagcaatt taaaaataty agcttaaaaa gtaaaactaa cggtagcgta   780
attaarttat ctgatgttgc caatgtagaa ataggytcac argcatataa ctttgccatt   840
ttggaaaatg gtaagcctgc taccgcggcw gcaattcaat taagcccggg wgctaacgcc   900
gtgaaaactg ccgaagktgt tcgagcaaaa attgaagart tgaagctaaa tttaccggaa   960
ggcatggart ttagtattcc ttacgacacc gcgccgtttg tcaaaatttc aattgaaaag  1020
gtaattcata cattacttga agccatggtt ctggttttca ttgtgatgta tctattttta  1080
cayaatgtcc gctatacgct tattccagcr attgtggcgc ctattgcctt actcggtact  1140
tttaccgtga tgttgcttgc cggcttttca attaacgtac tcaccatgtt cggtatggtg  1200
cttgccatcg ggattattgt cgacgatgcc attgtygtsg ttgaaaacgt mgaaaggatt  1260
atggcgacag aaggattatc gcctaaagat gcaacctcta aagcaatgaa agarattacc  1320
agcccgatta ttggtattac gctggtattg gcggcagtat ttttacctat ggcatttgcg  1380
agtggttctg taggggtaat ctataaacag tttaccttga ccatgtcggt atctatttta  1440
tttttcagcgc tattggcact yattttaaca ccggcacttt gtgccacgat tttaaarcca  1500
atcgatgggc atcaycagaa gaagggsttc tttgcatggt ttgaccgtag tttcgataaa  1560
gtcactaaaa agtatgaatt gatgctgctt aaaatcatca acatacagt tccaatgatg  1620
gtgatctttt tagtaattac cggtattacc tttrccggaa tgaaatattg gccaacagca  1680
tttatgccag aggaagatca aggytggttc atgacttcgt tccarctacc ttcagatgca  1740
acygcwgagc gtayycggaa ygtagtcaat caatttgaaa ataatttgaa agayaatccc  1800
gatgtaaaaa gtaataccac catttttggga tggggtttta gtggcgcagg acaaaaygta  1860
gctgtggcwt ttacracact taaagayttc aaagarcgga ctagctctgc atcyaagatg  1920
acaagcgmcg ttaatwcttc tatggcgaay agyacrgaag gygaracyat ggcbgtwttw  1980
cmaccygcwa ttgatgaryt rggtacttty tcwggyttya gyttrcgttt acaagaycgy  2040
gctaacttag gtatgcctgc tttaytggct gctcaagatg aacttatggc aatggcagcc  2100
aagaataaaa agttctatat ggtttggaat gaagggttgc cacaaggtga caatatttct  2160
ttaaaaattg accgtgaaaa gcttagtgca ytkggtgtta agttttctga tgtttcagac  2220
atcatytcta catcaatggg ttcaatgtat atcaatgact ccctaatcag aggacgtatg  2280
caacaagtca ttgtacargt tgagrctaaa tcacgtatgc aaytsaaaga tatcttgaat  2340
```

-continued

```
ytgaaagtca tgggttcwag cggtcaatta gtytcrttat cagaagttgt aacrccmcaa   2400
tggaataagg caccrcaaca atataatcgt tayaacggac gaccatcttt gagtattgct   2460
ggtattccta acttcgatac stcatcgggt gaagcaatgc gtgaaatgga acaactgatt   2520
gcgaaattac cgaaaggtat tggctacgag tggacaggta tttccttaca ggaaaagcag   2580
tctgaatcac aaatggcctt tttacttggt ttatcmatgy tmgttgtytt cctygtmttg   2640
gctgcactct atgaaagctg ggcaattcca ctttctgtga tgctrgttgt gccactcggt   2700
atttttggag caatcattgc cattatgtct agrgggttaa tgaatgatgt gttcttcaaa   2760
atcgggctaa ttaccattat tggtctatcg gcaaagaatg crattttgat tgttgaattt   2820
gcgaaaatgc traaagarga aggcatgagt ttgattgaag ccactgttgc cgcagccaaa   2880
cttcgcttac grccaatyct ratgacwtcw cttgcattta cgtgtggtgt aattcctttg   2940
gtkattgcmw caggtgcaag ttcagaaact caacatgctt taggcacagg ggtttttggy   3000
ggcatgattt cagcmaccat tctggctatt ttctttgttc ccgtgttttt tatcttcatt   3060
ttgggtgcag tagaaaagct attttcctct aagaaaaaaa tctcatcyta a            3111

<210> SEQ ID NO 64
<211> LENGTH: 2256
<212> TYPE: DNA
<213> ORGANISM: Bordetella pertussis
<220> FEATURE:
<221> NAME/KEY: misc_feature
<222> LOCATION: (1)..(2256)
<223> OTHER INFORMATION: Tcf gene ; genbank accession No. AY375533,
      BX640414, U16754

<400> SEQUENCE: 64
tcgacgccag cctgccaaga cggtctctgt cccggggcgg gaggctcact gagcctctcg     60
cgcaggtgcg tgtgtttcgt gcgtggatgg cgcttatttc ctttgtattg gttcgcagct    120
tcgttttgca ggcatggcga gtgcaacggg aaataaaggg tgcgtctgat agttgggcag    180
tggtggtgtg tagacactca ccgacagcaa tgggaggacg ggtgcgtcat ccgcgacgtg    240
cggcggttct ccacattgat tcaggccgct tcttgcgcgt cgtgtcttcc ggcagcggga    300
gcgtcaatcc ccttgagacc agaacctatg cacatttacg gaaatatgaa tcgagcaaca    360
ccttgccgcg gtgcggtgcg tgcccttgcg cttgccctgc tgggagcggg tatgtggaca    420
ctttctcctc cctcggcatg ggcgcttaag ctcccgtcgc tgctgacgga cgacgagctg    480
ragctggttc tgccgactgg catgtctctg gaggatttca agcgcagcct tcaggagtcc    540
gcgccgagcg cgctggcaac gccgccgtcg tcttcgcctc cggttgcgaa gccaggtccg    600
ggctccgttg ccgaggctcc gtcggggtcg ggccacaagg acaacccatc ccctcccgtc    660
gtcggcgtcg gtccaggtat ggcggagtcg tctggcggac ataaccccgg cgtggggggg    720
ggcacgcatg aaaatgggtt gcccggtata ggaaaggtcg gcgggtctgc gcccggaccg    780
gataccagta cgggctcggg tcccgacgcc ggcatggcgt ccggagcggg ttcgacgtcg    840
cccggcgyat cgggtgcgat gccgccctcg gaaggcgaga ggccggactc cggtatgtcc    900
gattcggggc ggggtggcga atcgtcggct ggaggcttga atccggacgg cgctggcaag    960
ccaccgcggg aggaaggcga gccgggttcc aagtctcctg cggacggtgg ccaggacggg   1020
ccgccgccgc cccgggacgg cggcgatgcg gatccgcaac ctccgcggga cgatggcaat   1080
ggggaacagc agccgcccaa gggcggcggg gatgaggggc agcgcccgcc gcctgccgcc   1140
ggaaacggtg gcaacggtgg caacgggaac gcgcagcttc ccgagcgcgg cgacgacgcg   1200
```

| | |
|---|---|
| ggtccgaagc ctcccgaggg agagggcggc gatgaaggtc cgcaaccgcc gcagggcggc | 1260 |
| ggcgagcagg acgcgccgga ggttcctccc gtcgcgccgg cgccgcccgc gggcaacggt | 1320 |
| gtctatgacc cgggcacgca taccttgacc acgccggcct ctgcggcggt gagcctggcc | 1380 |
| agcagttcgc atggcgtatg gcaggccgag atgaacgcgt tgagcaagcg catgggcgag | 1440 |
| ttgcgcctga cgccggttgc gggcggcgta tggggccgcg cttttggccg gcgccaggac | 1500 |
| gtcgacaacc gcgtgtcgcg cgagttccgc cagaccatca gcggtttcga actgggcgcc | 1560 |
| gataccgcct tgccggtggc cgacgggcgc tggcacgtgg gcgcggtggc tggctacacc | 1620 |
| aacggccgca tcaagttcga ccggggcggc acgggcgatg acgacagcgt gcacgtgggc | 1680 |
| gcttacgcta cctacatcga ggacggcggt ttctatatgg atggcatcgt gcgggtcagc | 1740 |
| cgcattcgcc acgcgttcaa ggtggacgac gccaagggcc ggcgcgtgcg cggccagtac | 1800 |
| cgcggcaatg gcgtgggcgc gtcgctggaa ctgggcaagc gcttcacgtg gcccggcgcc | 1860 |
| tggtacgtgg agccgcagct ggaggtggcc gccttccatg cgcaagggc cgactacacc | 1920 |
| gccagcaacg gcctgcgcat caaggacgac ggcacgaact ccatgctggg ccgcctgggc | 1980 |
| ctgcacgtgg ggcggcagtt cgacctgggc gatggccgcg tggtgcagcc ctacatgaag | 2040 |
| ctgagctggg tgcaggagtt cgacggcaag ggcacggtgc gcaccaacga catccggcac | 2100 |
| aaggtgcggc tcgatggcgg ccgcaccgaa ctggccgtag gggtggcttc gcaactgggc | 2160 |
| aagcacggca gcctgttcgg ctcgtacgag tacgccaagg gcagccgcca gaccatgccg | 2220 |
| tggaccttcc acgtcggcta tcgctacgcc tggtag | 2256 |

<210> SEQ ID NO 65
<211> LENGTH: 1170
<212> TYPE: DNA
<213> ORGANISM: Chlamydophila pneumoniae
<220> FEATURE:
<221> NAME/KEY: misc_feature
<222> LOCATION: (1)..(1170)
<223> OTHER INFORMATION: Genbank accession
      nos. AE017159, AE002161, DQ358972, AE001363, BA000008, AF131889,
      AY555078, L04982, M73038; Omp gene

<400> SEQUENCE: 65

| | |
|---|---|
| atgaaaaaac tcttaaagtc ggcgttatta tccgccgcat tgctggttc tgtyggctcc | 60 |
| ttacaagcct tgcctgtagg gaaccettct gatccaagct tattaattga tggtacaata | 120 |
| tgggaaggtg ctgcaggaga tccttgcgat ccttgcgcta cttggtgcga cgctattagc | 180 |
| ttacgtgctg gattttacgg agactatgtt ttcgaccgta tcttaaaagt agatgcacct | 240 |
| aaaacatttt ctatgggagc caarcctact ggatccgctr ctgcaaacta tactactgcs | 300 |
| gtagatagac ctaaccckgc ctacaataag catttacacg atgcagagtg gttcactaat | 360 |
| gcaggcttca ttgccttaaa catttgggat cgctttgatg ttttctgtac yttaggagct | 420 |
| tctaatggtt acattaragg aaactctaca gcgttcaatc tcgttggttt attcggagtt | 480 |
| aaaggtactw ctgtarmtgc aaatgaacta ccaaacgttt ctttaagtaa yggagttgtt | 540 |
| gaactytaca cagacacctc tttctcttgg agcgtaggcg ctcgtggagc yttatgggaa | 600 |
| tgcggttgtg caactttggg agctgaattc caatatgcac agtccaaacc taaagttgaa | 660 |
| gaacttaatg tgatctgtaa cgtakckcaa ttctctgtaa acaaacccaa gggctataaa | 720 |
| ggcgttgctt tcccttgcc aacagacgct ggcgtagcaa cagctactgg aacaaagtct | 780 |
| gcgaccatca attatcatga atggcaagta ggagcctctc tatcttayag actaaactct | 840 |
| ttagtgccat acattggagt acaatggtct cgagcaactt tgatgctga taacatccgc | 900 |

| | |
|---|---|
| attgctcagc caaaactacc tacagctgtt ttaaacttaa ctgcatggaa ccctycttta | 960 |
| ctaggaaatr csacrrcatt gyctactast gattcgttct cagacttcat gcaaattgtt | 1020 |
| tcctgtcaga tcaacaagtt taaatctaga aaagcttgtg gagttactgt aggagctact | 1080 |
| ttagttgatg ctgataaatg gtcacttact gcagaagctc gtttaattaa cgagagagct | 1140 |
| gctcacgwaw ctggtcagtt cagattctaa | 1170 |

<210> SEQ ID NO 66
<211> LENGTH: 1833
<212> TYPE: DNA
<213> ORGANISM: Enterobacter aerogenes
<220> FEATURE:
<221> NAME/KEY: misc_feature
<222> LOCATION: (1)..(1833)
<223> OTHER INFORMATION: Genbank accession no. Z26655; tsx gene

<400> SEQUENCE: 66

| | |
|---|---|
| gatatcaagc gccagcgcgc agtaagcgct cacgccgggc aaaacggccc ggcgcccgct | 60 |
| tttcatctat cgaagttatc catttacaac ttttcataag agttcattag aaatcgctcc | 120 |
| tgtaggcgat tttcagtagc attttgtcaa gaaatgcata gaatcgtgaa cgcaatcgat | 180 |
| tacgcatgtt ctggttatgt gaaacaacac gtattttgt gagcaatgat ttctataata | 240 |
| gacccccaca gaaagacgaa atatttagca acgcttcggc aattttctta acgccttttg | 300 |
| gcttaattta aacaatggca tcaacatgaa aaaacatta ctggcagcga gcgctgttgt | 360 |
| ggcgcttttcc gcttctttca ccgctggcgc ggcagaaact gaaaaaccgc agtacctgtc | 420 |
| tgattggtgg caccagagtg tgaacgtagt cggtagctac cacactcgtt ttggaccgca | 480 |
| gatccgtaac gatacctatc tggaatacga agcgtttgct aaaaaagatt ggtttgattt | 540 |
| ctacggctat attgatgcgc cggtcttctt cggcggcaac agcacggcga aggtatctg | 600 |
| gaacaaaggc tccccgctgt ttatggagat cgaaccgcgc ttctctatcg acaagctgac | 660 |
| caacaccgac ctgagcttcg ggccgttcaa agagtggtac ttcgcgaaca actatatcta | 720 |
| cgatatgggc cgcaacgact ctcaggagca gagcacctgg tatatgggtc tgggtaccga | 780 |
| catcgatacc ggtctgccga tgagcctgtc gctgaatatc tatgctaaat accagtggca | 840 |
| gaactacggc gcctccaacg aaaacgagtg ggacgcgtac cgcttcaagg tgaaatactt | 900 |
| cgttccgctg accgacctgt ggggcggttc gctgagctat attggcttca ccaacttcga | 960 |
| ctggggttct gaccttggcg acgacaactt ctacgatatg aacggtaagc acgcgcgtac | 1020 |
| cagcaactct atcgcgtcca gccacatcct ggcgctgaac tacgcgcact ggcactactc | 1080 |
| tatcgtcgcg cgttacttcc ataacggcgg ccagtgggct gatgatgcta agctgaactt | 1140 |
| cggcgacggc gacttcagcg ttcgctctac cggctggggt ggctacttcg ttgtcggtta | 1200 |
| caacttctaa ttgctgatac agcaagacag cgcccgggac gcgttttacg cttaccgact | 1260 |
| gttttttat cgctccccac atctcacctt acgtaagaaa tcgctcagtg aacggtcggc | 1320 |
| gcactcgctg aaacgacgtt cgatcacctt cacctccaga caacgatcga dacgaaagtt | 1380 |
| acgataatca ctgcgcagtt cgcaccaggc caccagcagc aacgctccc cccagaaaaa | 1440 |
| tagccccagc ggcagcactt cacgcgcgta cctgccagat catcctgata gtaagctgca | 1500 |
| acacctgctg attggatcgg cctgatggat aacgtcaaaa tgggtttag cattaacgta | 1560 |
| gcgcgccaag gtcagggcaa acagccgggt ctcgtccgct ttgcgccgcc ggtcttccgg | 1620 |
| caaaatcgcc agcatttttt cctgagctga ctccaacgac tgcgaaagcg catctccgcc | 1680 |

```
ccaggtcttc agtagtcgaa tcgcggcgat tagcgcttcg gattgtttgc tggtcagcat    1740
cagcggcggc agatgatagc ccgccagcag acgataaccg ctcccggcct cgccctcaac    1800
cggtacaccg gagagcgaga ggtcgcggat atc                                 1833
```

<210> SEQ ID NO 67
<211> LENGTH: 1041
<212> TYPE: DNA
<213> ORGANISM: Enterobacter cloacae
<220> FEATURE:
<221> NAME/KEY: misc_feature
<222> LOCATION: (1)..(1041)
<223> OTHER INFORMATION: Genbank accession nos. Y13230, AJ422108; rpoS
      gene

<400> SEQUENCE: 67

```
atgccagcca gggtgtctcg tccagggatc acgggtagga gccaccttat gagtcagaat      60
acgctgaaag ttcatgattt aaatgaagac gcggaatttg atgagaacgg agcagaggct     120
tttgacgaaa aagccttagt agaagaggaa cccagtgata acgatttggc tgaagaagag     180
ctgttatcgc agggtgccac acagcgtgtg ctggacgcga ctcagcttta ccttggggag     240
attggttact ccccactgct aacggccgaa gaagaagtct atttcgcacg tcgtgctttg     300
cgtggtgatg ttgcctcgcg tcgtcgcatg atcgaaagta acctgcgact ggtcgtgaaa     360
attgcccgcc gttacggcaa tcgtggtctg gctctgctgg atctgattga agagggcaac     420
ttaggtctca tccgcgcagt tgagaagttt gacccggaac gcgggttccg tttctcaacc     480
tacgcgacct ggtggattcg tcagaccatc gaacgggcta ttatgaacca gacccgtacg     540
attcgactgc cgatccacat cgtcaaagag ttgaatgttt atctgcgtac cgcgcgcgag     600
ttgtcccata aactggacca cgagccaagt gcggaagaga ttgcagagca actcgacaaa     660
ccggttgatg acgtaagccg tatgctgcgt ctcaacgagc gcattacctc ggttgacacc     720
ccgctgggtg gcgactccga aaaagcgctg ctggacattc tggccgatga aaaagacaac     780
ggcccggaag acaccacgca ggacgatgac atgaaacaga gcatcgtcaa atggctgttc     840
gaactgaacg ccaaacagcg tgaagtgctg gcacgtcgtt tcggtttact ggggtatgaa     900
gctgcgacac tggaagacgt cggtcgtgag attggcctga cccgtgaacg tgttcgtcag     960
attcaggttg aaggactacg ccgcctgcgt gaaatcctgc aagggcaagg tctgaatatc    1020
gaagcgctgt tccgcgagta a                                              1041
```

<210> SEQ ID NO 68
<211> LENGTH: 1030
<212> TYPE: DNA
<213> ORGANISM: Escherichia coli
<220> FEATURE:
<221> NAME/KEY: misc_feature
<222> LOCATION: (1)..(1030)
<223> OTHER INFORMATION: Genbank accession nos. AP009048, U00096,
      U00039, X67639, CP000802, BA000007, CP000468, CP000243, AE005174,
      CP000247, CP000800, AE014075; uspA gene

<400> SEQUENCE: 68

```
ctcccgatac gctgccaatc agttaacacc aggtcctgga gaaaccgctt ttgtggtgac      60
caacatacga gcggctctat agatagtgta ggagatcagg ttgttttttt tccagaaggt     120
taaccactat caatatattc atgtcgaaaa tttgtttatc taacgagtaa gcaaggcgga     180
ttgacggatc atccgggtcg ctataaggta aggatggtct taacactgaa tctttacggc     240
tgggttagcc ccgcgcacgt agttcgcagg acgcgggtga cgtaacggca caagaaacgc     300
```

```
tagctggcca gtcatcgaca actttatgga aggagtaaca ctatggctta taaacacatt      360
ctcatcgcgg tcgayctctc cccggaaagc aaagttctgg tagagaaagc agtctctatg      420
gctcgcccmt acaatgcgaa agtttctctg atccacgtag atgtaaacta ctctgaccta      480
tayaccgggc ttatygatgt gaatctkggt gatatgcaga aacgcatctc tgaagagaca      540
catcatgcrc tgaccgagct ttcmacycaat gcaggctacc caatcactga aaccctgagc      600
ggcagcggcg ayctgggcca ggtwctggtc gatgcaatca agaaatacga tatggatytr      660
gtggtttgtg gtcaccacca ggacttctgg agcaaactga tgtcttccgc acgtcagctg      720
atcaacaccg ttcacgttga tatgctgatt gttccgctss ssgacgaaga agaataatct      780
tccctcyacg acgtgttcct gaacgcccgc atatgcgggc gttttgcttt ttggcgcgcc      840
ttgttacctg atcatcgtaa acaccttatc tggcctacgg tctgcgtacg caatcaaaat      900
ccccagccaa tacaacattt aacaccatca tattttccat cattagtgtg atcatctggt      960
tattttctgt tgtaatagtg tattaatcta ttcaccgcat caatattaag aatctctgac     1020
agatgtaaac                                                            1030
```

<210> SEQ ID NO 69
<211> LENGTH: 1128
<212> TYPE: DNA
<213> ORGANISM: Klebsilla pneumonia
<220> FEATURE:
<221> NAME/KEY: misc_feature
<222> LOCATION: (1)..(1128)
<223> OTHER INFORMATION: Genbank accession nos. AY823268, CP000647,
      AF146532; Wab gene

<400> SEQUENCE: 69

```
atgagtaaat tcaggctggc tctggtgcgg cagaagtacc gcccggacgg cggcgcagaa        60
cggtttgtct cccgcgcgct ggaagccctc gacagcagtc atctgcaact gaacgtcatc       120
acccgcgaat ggcaggggcc ggtgaaaccg gactggcaga tccatatctg taacccacgt       180
aaatgggggc gcatcagccg cgagcgcagc tttgccaacg ccgcgcgcga gctctggcag       240
cgcgagtcct tcgacctggt gcagagccat gaacgtattc ccggctgcga tctctaccgc       300
gctggcgatg gcgttcatcg ccgctggctg cagcagcgct cgcgcatttt accggcctgg       360
aaaagccgcc tgctgttcgc cgaccgttac caccgctacg tcatgcaggc ggaacgcgag       420
atgtatgaag actcacacct gcgcggggtg atctgcaacg ccgagatgat caagcgcgag       480
attatcgaag actttggcct gccggcgag aagatccacg ttatttacaa cgccattgac       540
aaccagcgct tcctgccgcc agacgaagag acctttgccg ccttacgcgc caaatggcag       600
ctgccgctgc aggcgacctg cctgatctac gtcggctccg gctttgaacg taaagggctg       660
gcggcggcga ttcgcgccat cgcccctacc gatcgctacc tgctggtggt cggcaaagat       720
aaggatcagc ctcgctatca ggcgctggcg aagagcctga actgtggagc gcgggtgcgc       780
ttcttcggca tgcagtcgga gacattgccc ttctatcaaa tggccgatgg tctgctgctg       840
ccgacccttc acgatccgtt ccccaacgtc atcctcgagg caatggcctg cggtctgccg       900
gtgatcacca ctaccggctg cggcggggcg gagtttatcg tcgacggcca caacggttac       960
gtctgcgacg ctctggatat cccggcgcta cagcaggcgg taatggccct gcccgcgcgc      1020
gcgctgagct ccgcggaagg cggtcacgcc cgcgagcgca ttatggcctg caccagcgag      1080
cgactctcaa cccagctgct ttctctttat caggatctgg tgaattaa                   1128
```

<210> SEQ ID NO 70

-continued

<211> LENGTH: 705
<212> TYPE: DNA
<213> ORGANISM: Legionella pneumophilla
<220> FEATURE:
<221> NAME/KEY: misc_feature
<222> LOCATION: (1)..(705)
<223> OTHER INFORMATION: Genbank accession nos. AJ496268, AJ496272, CP000675, AE017354, CR628337, CR628336, AJ496381, AJ496273, AJ496271; Mip gene, n is a, t, g, and c

<400> SEQUENCE: 70

```
atgaagatga aawyggtgac tgcrgsknky vykgggctkg caatgtcaac agcaatggct     60
gyaascgatg ccacatcatt agctacwgac aaggataagt tgtcttatag cattggtgcc    120
gatttgggra agaayttaa raatcaaggc atwgatgtta ryccggaagc awtggctaaa    180
ggcatgcaag acgctatgag tggcgctcaa ttggctytaa ccgarcarca aatgaaagac    240
gttcttaaya artttcaraa agatttgatg gcwaarcgya cwgctgaatt caataaraar    300
gcrgatgaaa ataaagtrma aggggaagcc tttttaactg aaaacaaaaa caagccaggy    360
gttgttgtmt trccaagygg tttgcartay amagtratca ynctggraat ggygttaaac    420
cyggwaaatc bgatacagyb achrkssany ayctggtcny ctgattgatg gtaccgtttt    480
tgacagtacc gaaaaaacwg gtaagccagc hacdttycag gtttcrcaag tkatyccdgg    540
atggacwgar gctttrcmat tgatgmcmgc hggatcaacy tggaaattta tgttcchkcm    600
ggctygcwta tgghcccgan cnnnggcgga ccyattggcc craatgaaac tttaatatty    660
aaaattcact taatttcagt gaaaaaatca tctwartttt tttga                    705
```

<210> SEQ ID NO 71
<211> LENGTH: 2462
<212> TYPE: DNA
<213> ORGANISM: Moraxella catarrhalis
<220> FEATURE:
<221> NAME/KEY: misc_feature
<222> LOCATION: (1)..(2462)
<223> OTHER INFORMATION: Genbank accession nos. U69981, U69982, U83900, U83901, AY726666, L12346, U69980, AY726667; cop gene

<400> SEQUENCE: 71

```
tcaagcctca taatcggagt tatkrykaat aagtttcaat tattaccgmt gacattggcg     60
gtgagtgccg cttttacaac cactgctttt gcagctgtta gccagcctaa ggttgtcttg    120
gcaggcgata cagtggtcag tgatcgccaa ggtgcaaaaa ttaaaaccaa tgttgttacc    180
ttacgagaaa aagacgaaag cacggctaca gatttgcgtg gtttgttaca agatgaacct    240
gccatcggtt ttggcggtgg taatggtact tctcaatttr tcagcattcg tggcatgggt    300
cataatgcca ttgacctaaa aattgacaac gcttatcaag atggtcaatt acactaccac    360
caaggtcgct ttatgctaga cccccagatg gtcaaagtcg tttcggtaca aaaaggggca    420
ggctttgcca gtgcaggcat tggggcaacc aatggtgcga ttgttaccaa aaccttagat    480
gctgatgagc ttttaagaaa cagcgacaaa gattatggct ttaaagttgg tgcaggctta    540
tcaaccaaca aaggtcattc ttatcatggc agtgcctttg gtaaagcaca gacaggattt    600
ggtcaggtag atgcccttgt ctcttataat caagtaaatg acagygacta taaaggcggt    660
aaagggtaca ccaatctgtt gggcaatgat gtggttacaa gaagtgcctt ggataaatcc    720
agttaccttg tcaaggcagg gctaactgct ggcgatcatc gatttgtggt cagccatcta    780
aatgaagttc ataaaggcat tcgtggtgtg cgtgaagagt ttgacttcgc caatcgtgcc    840
ttgacrmtag ayataraaaa arawgrtaaa ayccktaccg aarcwgagct tywggcagar    900
```

```
ttarataamr awtatscagg ymagggytay aarcttggya rwaaaayamm wgatgrtaaw      960
aagtatmatg tggtygatgc caatggyara ywggtrsctr atttaratag gaacaaccca     1020
actcagcgtg aaacctacca gaagttaacy aaycttgaat ggacagstaa aaaccttggt     1080
ttkgcaaatg aagttactgc caatgtctat aagttagaac atggacgcaa ctcttctagc     1140
gatcaaggta acacctatat caccaaagat gtgcccaaag agataataga taatgttgat     1200
acaccatcaa acatgcatgt ggtagccaca ggggctaata ttaattttga taagaatttt     1260
amtcacagcc cattaaaagg ctttggtgtt gaccatactt tattaaaata tggcatcaac     1320
tatcgccatc aaammgctgt accgcccaga agtctaaaac ctggtgtggt gcatcaagaa     1380
aaaaccgatg ctggcattta tctagaagcg gttaaccaaa ttaatgactt taccatcaat     1440
acaggcgtgc gtgttgaccg ttttgacttt aaagccwtgg ryggtaaaaa ggttggaaaa     1500
accgacatca acccaagctt tggggtgatt tatgatgtca atcctaatct tagcgtcagc     1560
ggtaacctaa tctatgccac tcgyagycca cgctttgytg atgcyatcct aagccgtggt     1620
tatcgtggtg gtgtgattag tattgatgac aatgcaaaag cagaaaaagc rcgyaatacy     1680
gagatwggtt ttawctataa taatggacca tataccgcct ttggcagtta tttttggcag     1740
cgtgtggwta aygccagagc saccgctgat atawctcgtc atggtacmac agatgctaat     1800
ggtaagycta ttaaagtacc arcgcttggc amccaaggtc atcagaccaa ccaaggctat     1860
gagytgggyg taggytatac cgaaggtgcg tgcgtgcgcg tgctggcgtt gctyacagca     1920
mwccawccat gcacaatgtc amattkrryg gyaaycctga atatgccgyg cgtacaggtc     1980
gtacatggac agcagatgtc gcctatcgcc tgccaaaccc cagtgtagag cttggtgtga     2040
gacacacmtt ggttgaaggg gtagatgcca aagacacwtc yatcmtwagy ggtraakttr     2100
ryrawcttaa ccgtgaaggc tmtaatgtca gtgacatcta tgccaactgg aagccttatg     2160
gyaatgataa ggtgaatgta aactttgcgg tgaataatgt ctttaataaa aactatcgcc     2220
cacacactca gcgtgcttcc atagatacct tacctggggc aggtcgtgat ttccgtgttg     2280
gcgtgaactt cacttactaa tacttaccga tttatcggta taatactgaa cactcaagca     2340
cgcttgggtg ttcttttttat gggtatgagt ggataaaaac gataaaaaam smmwmkyrtm     2400
wyatwkwkwk kskmtawwrw kawaawwwwa wmwywwywsw kwtwwaaamm mcrcrywkks     2460
gc                                                                   2462
```

<210> SEQ ID NO 72
<211> LENGTH: 5147
<212> TYPE: DNA
<213> ORGANISM: Mycoplasma pneumoniae
<220> FEATURE:
<221> NAME/KEY: misc_feature
<222> LOCATION: (1)..(5147)
<223> OTHER INFORMATION: Genbank accession nos. U00089, M21519, M18639,
      AF289999, AF286371, AF290000, AF290001, AF290002, DQ383277,
      AB024618, X07191, U34795, X13087; P1 gene

<400> SEQUENCE: 72

```
aattccgtag taacggaatt aacgtacgcg aagtagcttt aaagtatggt ggcggggggtc      60 atattcaggc cagcggtgca gttcttaaaa gcaagcgcga cataattcgt gtagttcaag     120
attgccaaaa gcaaattgct gtataatttt taacaactat gcaccaaacc aaaaaaaactg     180 ccttgtccaa gtccacttgg attctcatcc tcaccgccac cgcctccctc gcgacgggac     240
tcaccgtagt gggacacttc acaagtacca ccacgacgct caagcgccag caatttagct     300
acacccgccc tgacgaggtc gcgctgcgcc acaccaatgc catcaacccg cgcttaaccc     360
```

-continued

```
cgtgaacgta tcgtaacacg agcttttcct ccctccccct cacgggtgaa atcccgggg     420
cgtgggcctt agtgcgcgac aacagcgcta agggcatcac tgccggcagt ggcagtcaac     480
aaaccacgta tgatcccacc cgaaccgaag cggctttgac cgcatcaacc acctttgcgt     540
tacgccggta tgacctcgcc gggcgcgcct tatacgacct cgattttcg aagttaaacc      600
cgcaaacgcc cacgcgcgac caaaccgggc agatcacctt taaccccttt ggcggctttg     660
gtttgagtgg ggctgcaccc caacagtgaa acgaggtcaa aaacaaggtc cccgtcgagg     720
tggcgcaaga cccctccaat ccctaccggt ttgccgtttt actcgtgccg cgcagcgtgg     780
tgtactatga gcagttgcaa aggggttgg gcttaccaca gcagcgaacc gagagtggtc      840
aaaatmmttc caccaccggg gcaatgtttg gcttgaaggt gaagaacgcc gaggcggaca     900
ccgcgragag caatgaaaaa ctccagggcg ctgaggccac tggttcttca accacatctg     960
gatctggcca atccacccaa cgtgggggtt cgtcagggga caccaaagtc aaggctttaa    1020
aaatagaggt gaaaaagaaa tcggactcgg aggacaatgg tcagctgcag ttrraaaaaa    1080
atgatctcgc caacgctccc attaagcgga gcgaggagtc gggtcagtcc gtccaactca    1140
aggcggacga ttttggtact gcccttcca gttcgggatc aggcggcaac tccaatcccg     1200
gttccccac cccctgaagg ccgtggcttg cgactgagca aattcacaag gacctcccca     1260
aatgatccgc ctcgatcctg attctgtacg atgcgcctta tgcgcgcaac cgtaccgcca    1320
ttgaccgcgt tgatcacttg gatcccaagg ccatgaccgc gaactatccg cccagttgaa    1380
gaacgcccaa gtgaaaccac cacggtttgt gggactgaaa ggcgcgcgat gttttgctcc    1440
aaaccaccgg gttcttcaac ccgcgccgcc accccgagtg gtttgatggc gggcagacgg    1500
tcgcggataa cgaaaagacc gggtttgatg tggataactc tgaaaacacc aagcagggct    1560
ttcaaaagga agctgactcc gacaagtcgg ccccgatcgc cctcccgttt gaagcgtact    1620
tcgccaacat tggcaacctc acctggttcg ggcaagcgct tttggtgttt ggtggcaatg    1680
gccatgttac caagtcggcc cacaccgcgc ctttgagtat aggtgtcttt agggtgcgct    1740
ataatgcaac tggtaccagt gctactgtaa ctggttgacc atatgcctta ctgttctcag    1800
gcatggtcaa caaacaaact gacgggttaa aggatctacc ctttaacaat aaccgctggt    1860
ttgaatatgt accaccggatg gcagttgctg gcgctaagtt cgttggtagg gaactcgttt    1920
tagcgggtac cattaccatg ggtgataccg ctaccgtacc tcgcttactg tacgatgaac    1980
ttgaaagcaa cctgaactta gtagcgcaag gccaaggtct tttacgcgaa gacttgcaac    2040
tcttcacacc ctacggatga gccaatcgtc cggatttacc aatcggggct tgaagtagta    2100
gtagtagtag tagtcacaac gcaccctact acttccacaa taaccccgat tgacaagacc    2160
gtccaatcca aaatgtggtt gatgcctta ttaagccctg agaggacaag aacggtaagg     2220
atgatgccaa atacatctac ccttaccgtt acagtggcat gtgagcttga caggtataca    2280
actggtccaa taagctcact gaccaaccat taagtgctga ctttgtcaat gagaatgctt    2340
accaaccaaa ctccttgttt gctgctattc tcaatccgga attgttagca gctcttcccg    2400
acaaggttaa atacggtaag gaaaacgagt ttgctgctaa cgagtacgag cgctttaacc    2460
agaagttaac ggtagctcct acccaaggaa caaactgatc ccacttctcc cccacgcttt    2520
cccgtttctc caccgggttc aaccttgtgg ggtcggtgct cgaccaggtg ttggattatg    2580
tgccctggat tgggaatggg tacaggtatg caataaccca ccgggcgtg gatgatataa       2640
ccgcgcctca aaccagcgcg gggtcgtcca gcggaattag trcgaacaca agtggttcgc    2700
```

```
gttcctytct cccgacgttt tccaacatcg gcgtcggcct caaagcgaat gtccaagcca    2760
ccctcggggg cagtcagacg atgattacag gcggttcgcc tcgaagaacc ctcgaccaag    2820
ccaacctcca gctctgaacg ggggcggggt gaaggaatga taaggcttca agtggacaaa    2880
gtgacgacca caccaagttc acgagcgcta cggggatggr ccagcaggra caatcaggta    2940
cctccgcggg gaatcccgac tcgttaaagc aggataakat tagtaagagt ggggatagtt    3000
taaccacgca ggacrgcaat gcgaysgrtc aacaagaggc cacyaactac accaacctcc    3060
cccccaacct caccccgacc gctgattgac cgaacgcgct gtcattcacc aacaagaaca    3120
acgcgcagcg cgcccagcts ttcctbcgcg gcytgttggg cagcatcccg gtgttggtka    3180
atmrrwsygg symmgatkmy aacaarttym argcsrmsga ccaaaaatgg tcctacaccg    3240
acttacaktc ggaccaaacc aaactgaacc tccccgctta cggtgaggtg aatgggttgt    3300
tgaatccggc gttggtggaa acctattttg ggaacacgcg agcgrgtggt tcggggtcca    3360
acacgaccag ttcacccggt atcggtttta aaattcccga acaaartray raytcsaarg    3420
cyrysctgat cacccccggg ttggcttgaa cgccscarga cgtyggtaac ctcgttgtca    3480
gtggcaccas sktsagcttc cagctcggcg ggtggytrgt yassttcacg gactttrtca    3540
aaccccgcgc kggttayyts ggbctccagt taaskggcyt ggatgcmagt gaygcgacca    3600
rmgbgmbytm atttgggccm mscggccctg agcggccttt cgtggcagtt gggtcaaccg    3660
gytgggccgc gtggagagtg tgtgggattt raagggggtg tgggcggatc aagctcagty    3720
sgmckcgcaa gsakctacma syrmmgcwwc mrggdmmgcy ttrscrsmkc acccgaatgc    3780
tttggcstwy carrtkagyk wkrysgamrm grrtkcktac arsbcmamyh mrrgytcsgg    3840
ycmaaacavy tcscyctacc tscayttgrt kaarcctaag aaagtyrmmm rmwcsrmcma    3900
rytmgacsas gryytwaaaa acctgttgga ccccaaccag gttcgcacca agctgcgcca    3960
aagcttyggt acagaccatt ccacccagcc ccaatcgctc aaaacaacga caccggtrtt    4020
tggrrcsakk agtggtaacm tyrgyagtgt gcttagtggt ggrggtgctg gaggggggttc    4080 ttcaggctca ggtcaatctg gygtggayct ctcccccgtt gaamrrgtga gtgggtggct    4140
tgtggggcag ttaccaagca cgagtgacgg aaacacctcc tccaccaaca acctcgcgcc    4200
taatactaat acggggaatg atgtggtggg ggttggtcga cttctgaaa gcaacgccgc    4260 aaagatgaay gacgatgttg atggtattgt acgcaccca ctcgctgaac tgttagatgg    4320
ggaaggacaa acagctgaca ctggtccaca aagcgtgaag ttcaagtctc ctgaccaaat    4380
tgacttcaac cgcttgttta cccacccagt caccgatctg tttgatccgg taactatgtt    4440
ggtgtatgac cagtacatac cgctgtttat tgatatccca gcaagtgtga rccctaaaat    4500
ggttcgttta aaggtcttga gctttgacac caacgaacag agcttaggtc tccgcttaga    4560 gttcttttaaa cctgatcaag atacccaacc aaacaacaac gttcaggtca atccgaataa    4620
cggtgacttc ttaccactgt taacggcctc cagtcaaggt ccccaaacct tgtttagtcc    4680
gtttaaccag tgacctgatt acgtgttgcc gttagcgatc actgtaccta ttgttgtgat    4740
tgtgctcagt gttaccttag gacttgccat tggaatccca atgcacaaga acaaacaggc    4800
cttgaaggct gggtttgcgc tatcaaacca aaaggttgat gtgttgacca agcggttgg     4860 tagtgtcttt aaggaaatca ttaaccgcac aggtatcagt caagcgccaa aacgcttgaa    4920
acaaaccagt gcggctaaac caggagcacc ccgcccacca gtaccaccaa agccagggc     4980 tcctaagcca ccagtgcaac cacctaaaaa acccgcttag tatttatgaa atcgaagcta    5040
aagttaaaac gttatttact gttttttacca cttttaccgc taggacgttg tcactagcca    5100
```
acacctacct cctccaagac cacaacaccc tcaccccta cacgccc        5147

<210> SEQ ID NO 73
<211> LENGTH: 2012
<212> TYPE: DNA
<213> ORGANISM: Pseudomonas aeruginosa
<220> FEATURE:
<221> NAME/KEY: misc_feature
<222> LOCATION: (1)..(2012)
<223> OTHER INFORMATION: Genbank accession nos. K01397, AE004091,
      CP000438; Eta gene

<400> SEQUENCE: 73

| | |
|---|---|
| cacctgatac cccattggat ccccctggtc gccagcctcg gcctgctcgc cggcggctcg | 60 |
| tccgcgtccg ccgccgagga agccttcgac ctctggaacg aatgcgccaa agcctgcgtg | 120 |
| ctcgacctca aggacggcgt gcgttccagc cgcatgagcg tcgacccggc catcgccgac | 180 |
| accaacggcc agggcgtgct gcactactcc atggtcctgg agggcggcaa cgacgcgctc | 240 |
| aagctggcca tcgacaacgc cctcagcatc accagcgacg gcctgaccat ccgcctcgaa | 300 |
| ggcggcgtcg agccgaacaa gccggtgcgc tacagctaca cgcgccaggc gcgcggcagt | 360 |
| tggtcgctga actggctggt accgatcggc cacgagaagc cctcgaacat caaggtgttc | 420 |
| atccacgaac tgaacgccgg caaccagctc agccacatgt cgccgatcta ccatcgcgag | 480 |
| atgggcgacg agttgctggc gaagctggcg cgcgatgcca ccttcttcgt cagggcgcac | 540 |
| gagagcaacg agatgcagcc gacgctcgcc atcagccatg ccggggtcag cgtggtcatg | 600 |
| gcccagaccc agccgcgccg ggaaaagcgc tggagcgaat gggccagcgg caaggtgttg | 660 |
| tgcctgctcg acccgctgga cggggtctac aactacctcg cccagcaacg ctgcaacctc | 720 |
| gacgatacct gggaaggcaa gatctaccgg gtgctcgccg gcaacccggc gaagcatgac | 780 |
| ctggacatca aacccacggt catcagtcat cgcctgcact ttcccgaggg cggcagcctg | 840 |
| gccgcgctga ccgcgcacca ggcttgccac ctgccgctgg agactttcac ccgtcatcgc | 900 |
| cagccgcgcg gctgggaaca actggagcag tgcggctatc cggtgcagcg gctggtcgcc | 960 |
| ctctacctgg cggcgcggct gtcgtggaac caggtcgacc aggtgatccg caacgccctg | 1020 |
| gccagccccg gcagcggcgg cgacctgggc gaagcgatcc gcgagcagcc ggagcaggcc | 1080 |
| cgtctggccc tgaccctggc cgccgccgag agcgagcgct tcgtccggca gggcaccggc | 1140 |
| aacgacgagg ccggcgcggc caacgccgac gtggtgagcc tgacctgccc ggtcgccgcc | 1200 |
| ggtgaatgcg cgggcccggc ggacagcggc gacgccctgc tggagcgcaa ctatcccact | 1260 |
| ggcgcggagt tcctcggcga cggcggcgac gtcagcttca gcacccgcgg cacgcagaac | 1320 |
| tggacggtgg agcggctgct ccaggcgcac cgccaactgg aggagcgcgg ctatgtgttc | 1380 |
| gtcggctacc acggcacctt cctcgaagcg cgcaaagca tcgtcttcgg cggggtgcgc | 1440 |
| gcgcgcagcc aggacctcga cgcgatctgg cgcggtttct atatcgccgg cgatccggcg | 1500 |
| ctggcctacg gctacgccca ggaccaggaa cccgacgcac gcggccggat ccgcaacggt | 1560 |
| gccctgctgc gggtctatgt gccgcgctcg agcctgccgg gcttctaccg caccagcctg | 1620 |
| accctggccg cgccggaggc ggcgggcgag gtcgaacggc tgatcggcca tccgctgccg | 1680 |
| ctgcgcctgg acgccatcac cggccccgag gaggaaggcg ggcgcctgga gaccattctc | 1740 |
| ggctggccgc tggccgagcg caccgtggtg attccctcg cgatccccac cgacccgcgc | 1800 |
| aacgtcggcg gcgacctcga cccgtccagc atccccgaca aggaacaggc gatcagcgcc | 1860 |
| ctgccggact acgccagcca gccgggcaaa ccgccgcgcg aggacctgaa gtaactgccg | 1920 |

-continued

```
cgaccggccg gctcccttcg caggagccgg ccttctcggg gcctggccat acatcaggtt      1980
ttcctgatgc cagcccaatc gaatatgaat tc                                    2012

<210> SEQ ID NO 74
<211> LENGTH: 1119
<212> TYPE: DNA
<213> ORGANISM: Streptococcus pneumoniae
<220> FEATURE:
<221> NAME/KEY: misc_feature
<222> LOCATION: (1)..(1119)
<223> OTHER INFORMATION: Genbank accessin nos. CP000410, AE008540,
      Z34303, M13812, AE005672; lytA gene

<400> SEQUENCE: 74
ttgacttctt ttatatgata taataaagta tagtatttat gaaaaggaca tatagagact        60
gtaaaaatat acttttgaaa agcttttttag tctggggtgt tattgtagat agaatgcaga     120
ccttgtcagt cctatttaca gtgtcaaaat agtgcgtttt gaagttctat ctacaagcct     180
aatcgtgact aagattgtct tctttgtaag gtagaaataa aggagtttct ggttctggat     240
tgtaaaaaat gagttgtttt aattgataag gagtagaata tggaaattaa tgtgagtaaa     300
ttaagaacag atttgcctca agtyggcgtg caaccatata ggcaagtaca cgcacactca     360
actgggaatc cgcattcaac cgtacagaat gaagcggatt atcaytggcg gaaagaccca     420
gaattaggtt ttttctsgca yattgttggg aacggwtgca tcatgcrggt aggacctgtt     480
rataatggtg cctggsacgt tgggggcggk tggaatgctg aracctatgc agcggttgaa     540
ctgattgaaa gccattcaac yaaagaagag ttcatgacgg actaccgyct ttatatcgaa     600
ctcttacgca atctagcaga tgaagcargt ttgccgaaaa cgcttgatac agggagttta     660
gctggaatta aaacgcacga gtattgcacg aataaccaac caaacaacca ctcagaccay     720
gtkgayccwt ayccwtayyt kgcwaaatgg ggcattagcc gtgagcagtt taagyatgat     780
attgagaacg gcttgamkat tgaaacaggc tggaagaaaa tcgctgakaa gtggtaytat     840
ttyraygwag aaggtgcmat gaagacaggc tgggtcaagt acaaggacac ttggtactac     900
ttagacgcta aagaaggcgc matggtatca aaygccttta tccagtcagc ggacggaaca     960
ggctggtact acctcaaacc agacggaaca ctggcagaya rrccagavtt cacagtagag    1020
ccagatggct tgattacagt aaaataataa tggaatgtct atcaaatcag aacagcgcat    1080
attattaggt cttgaaaaag cttaatagta tgcgttttc                           1119
```

METHOD AND COMPOSITIONS FOR DETECTING RESPIRATORY DISEASE-CAUSING BACTERIAL SPECIES

CROSS-REFERENCE TO RELATED PATENT APPLICATION

This application claims priority to Korean Patent Application No. 10-2006-0094673, filed on Sep. 28, 2006, in the Korean Intellectual Property Office, the disclosure of which is incorporated herein in its entirety by reference.

BACKGROUND OF THE INVENTION

1. Field of the Invention

The present invention relates to a primer set for amplifying target sequence(s) of twelve respiratory disease-causing bacterial species, a probe or probe set specifically hybridizing with target sequence(s) of twelve respiratory disease-causing bacterial species, a microarray immobilized with the probe or probe set, and a method of detecting one or more of twelve respiratory disease-causing bacterial species using the probe or probe set.

2. Description of the Related Art

Probes for the detection of respiratory disease-associated bacteria are currently known. For example, U.S. Pat. No. 5,830,654 discloses hybridization assay probes for *Haemophilus influenzae* comprised of an oligonucleotide of about 14-18 nucleotides. U.S. Pat. No. 5,525,718 discloses oligonucleotides selectively hybridizing with a specific gene (e.g., the entE gene) of *Staphylococcus aureus*. U.S. Pat. No. 6,001,564 discloses primers or probes specific to *Escherichia coli, Klebsiella pneumoniae, Pseudomonas aeruginosa, Proteus mirabilis, Streptococcus pneumoniae, Staphylococcus aureus, Staphylococcus epidermis, Haemophilus influenzae,* and *Moraxella catarrhalis*.

In spite of the above-described conventional techniques, no primer sets capable of amplifying target sequences found in respective specific virulence factor genes of twelve bacterial species known to be associated with respiratory disease are reported. Furthermore, no probes specific to the target sequences of the virulence factor genes of the twelve bacterial species are reported.

Two single strands of a nucleic acid comprised of nucleotides hybridize to form a double helical structure in which the two polynucleotide chains running in opposite directions are held together by hydrogen bonds between matched base pairs. In a case where a first single strand of a nucleic acid is sufficiently complementary to a second single strand of the nucleic acid, the two single strands are held together under conditions that promote their hybridization, thereby resulting in double-stranded nucleic acid. Under appropriate conditions, DNA/DNA, RNA/DNA, or RNA/RNA hybrids may be formed.

Broadly, there are two fundamental nucleic acid hybridization procedures. In one procedure, known as "in-solution" hybridization, both a "probe" nucleic acid sequence and a nucleic acid molecule of a test sample are free in solution. In the other procedure, the probe nucleic acid is usually immobilized on a solid substrate and the nucleic acid sequence of the test sample is free in solution.

A probe may be a single-stranded nucleic acid sequence which is complementary in some particular degree to a nucleic acid sequence ("target sequence") sought to be detected. A probe may be labeled. The use of nucleic acid hybridization as a procedure for the detection of particular nucleic acid sequences is disclosed in U.S. Pat. No. 4,851,330, and No. 5,288,611, the disclosures of which are incorporated herein in their entireties by reference.

SUMMARY OF THE INVENTION

The present invention provides a primer set capable of specifically amplifying target sequence(s) of twelve respiratory disease-causing bacterial species.

The present invention also provides a probe set for detecting one or more of the twelve respiratory disease-causing bacterial species, which is specific to the target sequence(s) amplified using the primer set.

The present invention also provides a microarray on which the probe set is immobilized.

The present invention also provides a method of detecting one or more of the twelve respiratory disease-causing bacterial species using the probe set.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

Figure 1A:
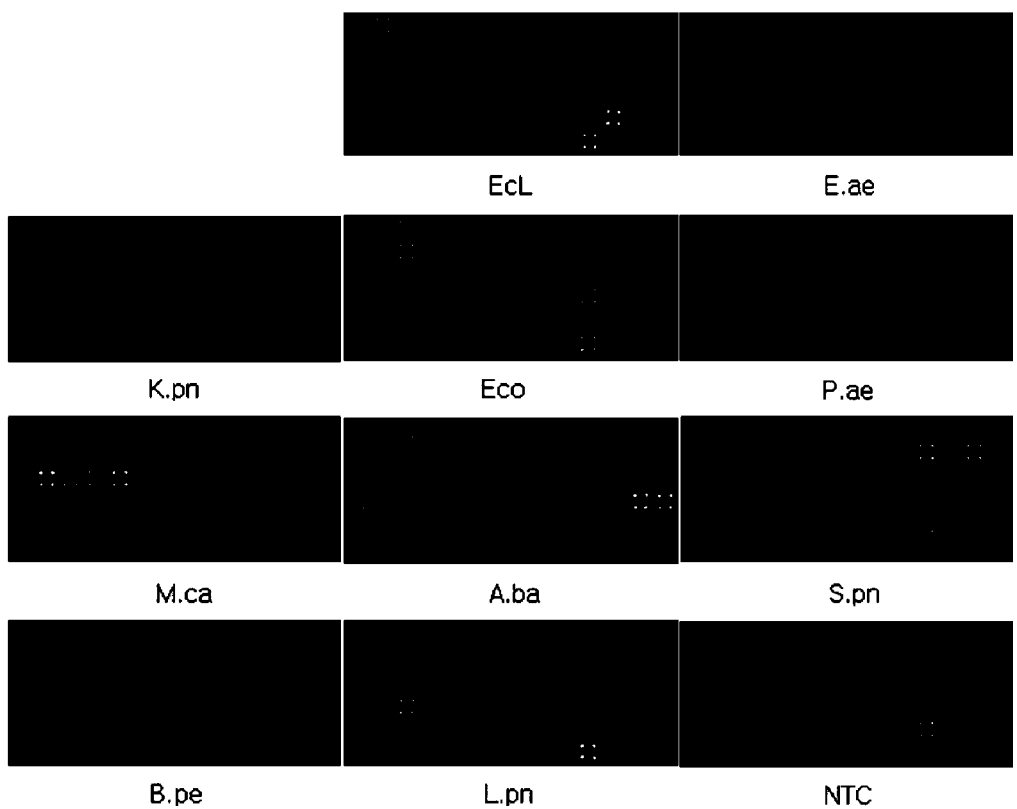
FIG. 1A presents images showing results of hybridization between PCR products (obtained by PCR using a primer set including all primer pairs specific to the respective virulence factor genes specifically expressed in ten bacterial species among the twelve bacterial species presented in Table 1, and genomic DNAs of the ten bacterial species, as templates) and oligonucleotide probes, immobilized on microarrays, which are specific to the virulence factor genes of the ten bacterial species and FIG. 1B schematically presents the layout of the oligonucleotide probes (identified by SEQ ID NOS) in the microarrays of FIG. 1A.
Figure 2:
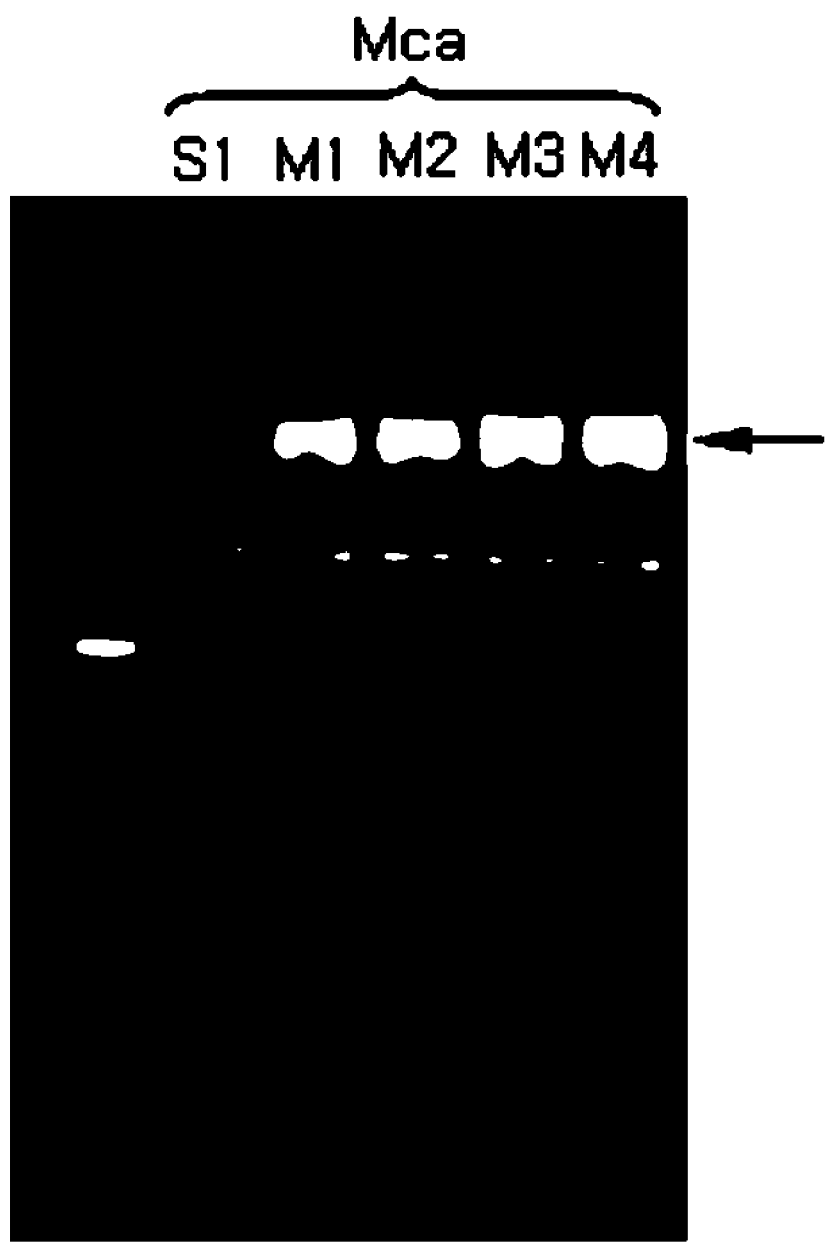
FIGS. 2 through 6 show the results of electrophoretic analysis of PCR products obtained by single PCR or multiplex PCR using ten primer sets, each specific to the virulence factor gene expressed in one of ten bacterial species.
Figure 3:
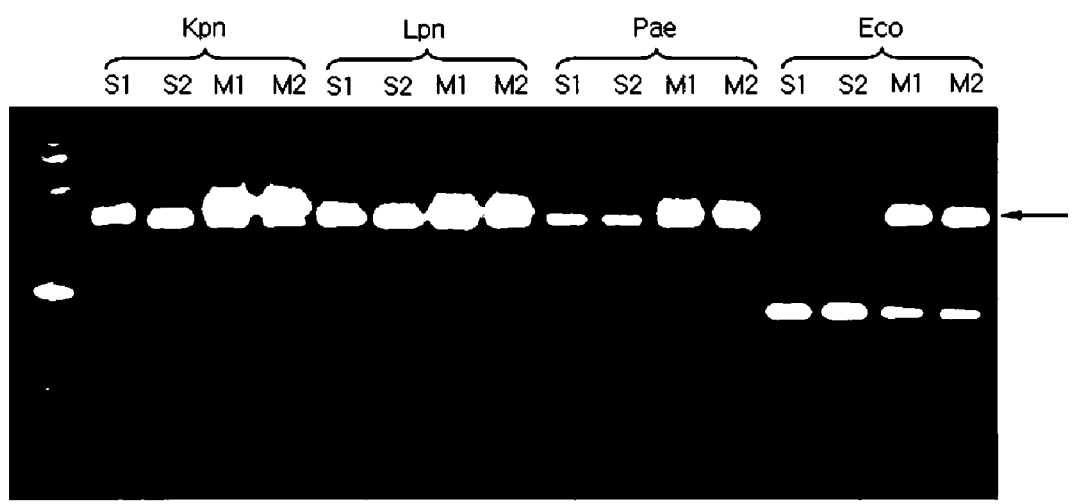
Figure 4:
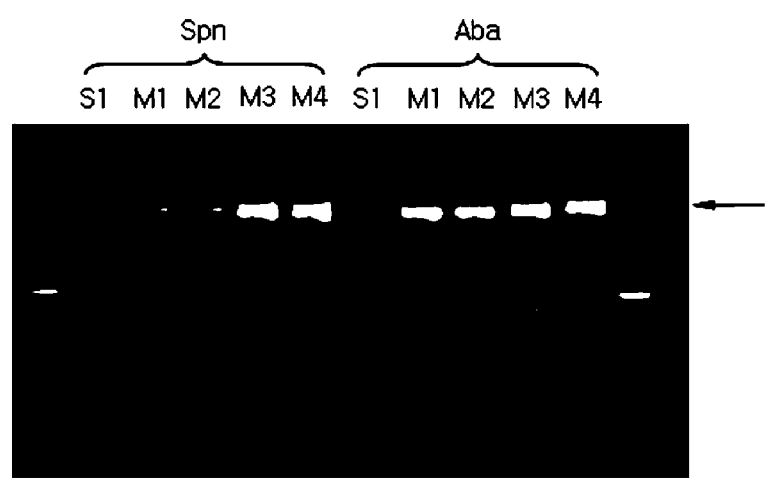
Figure 5:
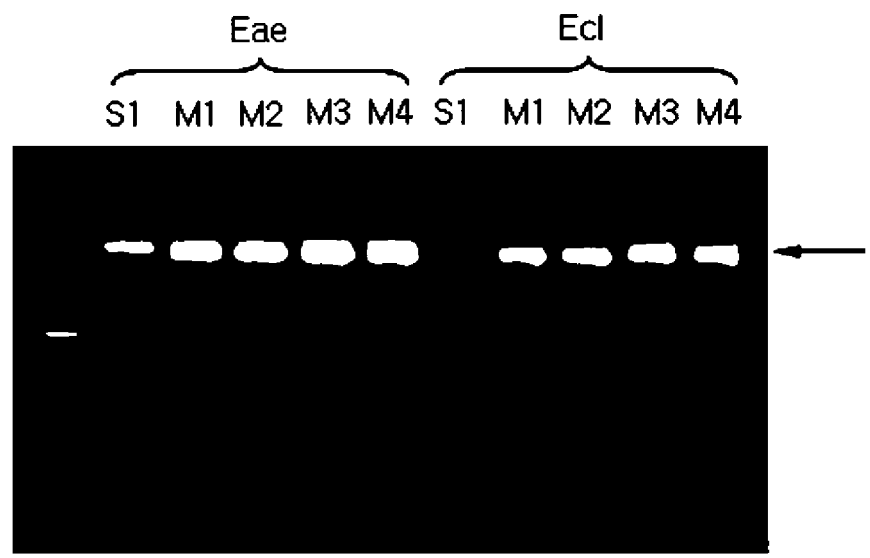
Figure 6:
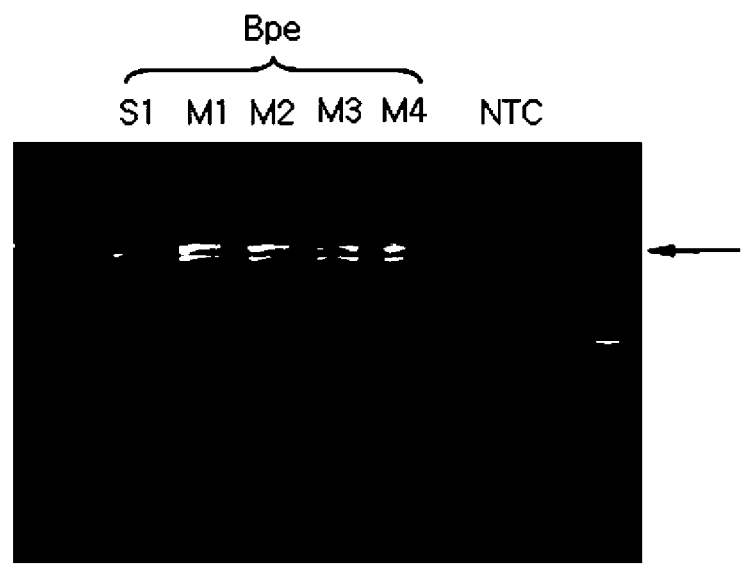

The present invention provides methods and compositions for detecting respiratory disease-causing bacterial species including *Acinetobacter baumannii, Bordetella pertussis, Chlamydophila pneumoniae, Enterobacter aerogenes, Enterobacter cloacae, Escherichia coli, Klebsiella pneumoniae, Legionella pneumophila, Moraxella catarrhalis, Mycoplasma pneumoniae, Pseudomonas aeruginosa,* and *Streptococcus pneumoniae*.

Disclosed herein is an oligonucleotide primer set for specifically amplifying at least one target sequence selected from the adeB gene of *Acinetobacter baumannii*, the Tcf (tracheal colonization factor) gene of *Bordetella pertussis*, the Omp (outer membrane protein) gene of *Chlamydophila pneumoniae*, the tsx (outer membrane protein, Tsx) gene of *Enterobacter aerogenes*, the rpoS (RNA polymerase accessory sigma factor) gene of *Enterobacter cloacae*, the uspA (universal stress protein A) gene of *Escherichia coli*, the Wab gene of *Klebsiella pneumoniae*, the Mip (major intrinsic protein) gene of *Legionella pneumophila*, the cop gene of *Moraxella catarrhalis*, the P1 gene of *Mycoplasma pneumoniae*, the ETA (exotoxin A) gene of *Pseudomonas aeruginosa*, and the lytA (murein hydrolase A) gene of *Streptococcus pneumoniae*. Thus, the primer set of the present invention can discriminate the twelve bacterial species based on the specific amplification products each individual primer pair was designed to amplify specifically.

In an embodiment, the oligonucleotide primer set comprises at least one oligonucleotide set selected from the group consisting of: an oligonucleotide set including at least one oligonucleotide selected from the group consisting of oligonucleotides which include at least 10 contiguous nucleotides present in a nucleotide sequence as set forth in SEQ ID NO: 1 and at least one oligonucleotide selected from the group consisting of oligonucleotides which include at least 10 contiguous nucleotides present in a nucleotide sequence as set forth in SEQ ID NO: 2; an oligonucleotide set including at least one oligonucleotide selected from the group consisting of oligonucleotides which include at least 10 contiguous nucleotides present in a nucleotide sequence as set forth in SEQ ID NO: 3 and at least one oligonucleotide selected from the group consisting of oligonucleotides which include at least 10 contiguous nucleotides present in a nucleotide sequence as set forth in SEQ ID NO: 4; an oligonucleotide set including at least one oligonucleotide selected from the group consisting of oligonucleotides which include at least 10 contiguous nucleotides present in a nucleotide sequence as set forth in SEQ ID NO: 5 and at least one oligonucleotide selected from the group consisting of oligonucleotides which include at least 10 contiguous nucleotides present in a nucleotide sequence as set forth in SEQ ID NO: 6; an oligonucleotide set including at least one oligonucleotide selected from the group consisting of oligonucleotides which include at least 10 contiguous nucleotides present in a nucleotide sequence as set forth in SEQ ID NO: 7 and at least one oligonucleotide selected from the group consisting of oligonucleotides which include at least 10 contiguous nucleotides present in a nucleotide sequence as set forth in SEQ ID NO: 8; an oligonucleotide set including at least one oligonucleotide selected from the group consisting of oligonucleotides which include at least 10 contiguous nucleotides present in a nucleotide sequence as set forth in SEQ ID NO: 9 and at least one oligonucleotide selected from the group consisting of oligonucleotides which include at least 10 contiguous nucleotides present in a nucleotide sequence as set forth in SEQ ID NO: 10; an oligonucleotide set including at least one oligonucleotide selected from the group consisting of oligonucleotides which include at least 10 contiguous nucleotides present in a nucleotide sequence as set forth in SEQ ID NO: 11 and at least one oligonucleotide selected from the group consisting of oligonucleotides which include at least 10 contiguous nucleotides present in a nucleotide sequence as set forth in SEQ ID NO: 12; an oligonucleotide set including at least one oligonucleotide selected from the group consisting of oligonucleotides which include at least 10 contiguous nucleotides present in a nucleotide sequence as set forth in SEQ ID NO: 13 and at least one oligonucleotide selected from the group consisting of oligonucleotides which include at least 10 contiguous nucleotides present in a nucleotide sequence as set forth in SEQ ID NO: 14; an oligonucleotide set including at least one oligonucleotide selected from the group consisting of oligonucleotides which include at least 10 contiguous nucleotides present in a nucleotide sequence as set forth in SEQ ID NO: 15 and at least one oligonucleotide selected from the group consisting of oligonucleotides which include at least 10 contiguous nucleotides present in a nucleotide sequence as set forth in SEQ ID NO: 16; an oligonucleotide set including at least one oligonucleotide selected from the group consisting of oligonucleotides which include at least 10 contiguous nucleotides present in a nucleotide sequence as set forth in SEQ ID NO: 17 and at least one oligonucleotide selected from the group consisting of oligonucleotides which include at least 10 contiguous nucleotides present in a nucleotide sequence as set forth in SEQ ID NO: 18; an oligonucleotide set including at least one oligonucleotide selected from the group consisting of oligonucleotides which include at least 10 contiguous nucleotides present in a nucleotide sequence as set forth in SEQ ID NO: 19 and at least one oligonucleotide selected from the group consisting of oligonucleotides which include at least 10 contiguous nucleotides present in a nucleotide sequence as set forth in SEQ ID NO: 20; an oligonucleotide set including at least one oligonucleotide selected from the group consisting of oligonucleotides which include at least 10 contiguous nucleotides present in a nucleotide sequence as set forth in SEQ ID NO: 21 and at least one oligonucleotide selected from the group consisting of oligonucleotides which include at least 10 contiguous nucleotides present in a nucleotide sequence as set forth in SEQ ID NO: 22; and an oligonucleotide set including at least one oligonucleotide selected from the group consisting of oligonucleotides which include at least 10 contiguous nucleotides present in a nucleotide sequence as set forth in SEQ ID NO: 23 and at least one oligonucleotide selected from the group consisting of oligonucleotides which include at least 10 contiguous nucleotides present in a nucleotide sequence as set forth in SEQ ID NO: 24.

In an embodiment, the oligonucleotide primer set comprises an oligonucleotide set selected from the group consisting of: an oligonucleotide set comprising an oligonucleotide consisting of at least 10 contiguous nucleotides present in a nucleotide sequence as set forth in SEQ ID NO: 1 and an oligonucleotide consisting of at least 10 contiguous nucleotides present in a nucleotide sequence as set forth in SEQ ID NO: 2; an oligonucleotide set comprising an oligonucleotide consisting of at least 10 contiguous nucleotides present in a nucleotide sequence as set forth in SEQ ID NO: 3 and an oligonucleotide consisting of at least 10 contiguous nucleotides present in a nucleotide sequence as set forth in SEQ ID NO: 4; an oligonucleotide set comprising an oligonucleotide consisting of at least 10 contiguous nucleotides present in a nucleotide sequence as set forth in SEQ ID NO: 5 and an oligonucleotide consisting of at least 10 contiguous nucleotides present in a nucleotide sequence as set forth in SEQ ID NO: 6; an oligonucleotide set comprising an oligonucleotide consisting of at least 10 contiguous nucleotides present in a nucleotide sequence as set forth in SEQ ID NO: 7 and an oligonucleotide consisting of at least 10 contiguous nucleotides present in a nucleotide sequence as set forth in SEQ ID NO: 8; an oligonucleotide set comprising an oligonucleotide consisting of at least 10 contiguous nucleotides present in a nucleotide sequence as set forth in SEQ ID NO: 9 and an oligonucleotide consisting of at least 10 contiguous nucleotides present in a nucleotide sequence as set forth in SEQ ID NO: 10; an oligonucleotide set comprising an oligonucleotide consisting of at least 10 contiguous nucleotides present in a nucleotide sequence as set forth in SEQ ID NO: 11 and an oligonucleotide consisting of at least 10 contiguous nucleotides present in a nucleotide sequence as set forth in SEQ ID NO: 12; an oligonucleotide set comprising an oligonucleotide consisting of at least 10 contiguous nucleotides present in a nucleotide sequence as set forth in SEQ ID NO: 13 and an oligonucleotide consisting of at least 10 contiguous nucleotides present in a nucleotide sequence as set forth in SEQ ID NO: 14; an oligonucleotide set comprising an oligonucleotide consisting of at least 10 contiguous nucleotides present in a nucleotide sequence as set forth in SEQ ID NO: 15 and an oligonucleotide consisting of at least 10 contiguous nucleotides present in a nucleotide sequence as set forth in SEQ ID NO: 16; an oligonucleotide set comprising an oligonucleotide consisting of at least 10 contiguous nucleotides present in a nucleotide sequence as set forth in SEQ ID NO: 17 and an oligonucleotide consisting of at least 10 contiguous nucleotides present in a nucleotide sequence as set forth in SEQ ID NO: 18; an oligonucleotide set comprising an oligonucleotide consisting of at least 10 contiguous nucleotides present in a nucleotide sequence as set forth in SEQ ID NO: 19 and an oligonucleotide consisting of at least 10 contiguous nucleotides present in a nucleotide sequence as set forth in SEQ ID NO: 20; an oligonucleotide set comprising an oligonucleotide consisting of at least 10 contiguous nucleotides present in a nucleotide sequence as set forth in SEQ ID NO: 21 and an oligonucleotide consisting of at least 10 contiguous nucleotides present in a nucleotide sequence as set forth in SEQ ID NO: 22; and an oligonucleotide set comprising an oligonucleotide consisting of at least 10 contiguous nucleotides present in a nucleotide sequence as set forth in SEQ ID NO: 23 and an oligonucleotide consisting of at least 10 contiguous nucleotides present in a nucleotide sequence as set forth in SEQ ID NO: 24.

In an embodiment of the primer set, the target sequence can be selected from a nucleotide region from position 126 to 227 of the adeB gene (SEQ ID NO: 63) of *Acinetobacter baumannii*, a nucleotide region from position 64 to 428 of the Tcf gene (SEQ ID NO: 64) of *Bordetella pertussis*, a nucleotide region from position 413 to 622 of the Omp gene (SEQ ID NO:65) of *Chlamydophila pneumoniae*, a nucleotide region from position 1267 to 1689 of the tsx gene (SEQ ID NO: 66) of *Enterobacter aerogenes*, a nucleotide region from position 797 to 912 of the rpoS gene (SEQ ID NO: 67) of *Enterobacter cloacae*, a nucleotide region from position 855 to 976 of the uspA gene (SEQ ID NO: 68) of *Escherichia coli*, a nucleotide region from position 89 to 419 of the Wab gene (SEQ ID NO: 69) of *Klebsiella pneumoniae*, a nucleotide region from position 105 to 469 of the Mip gene (SEQ ID NO: 70) of *Legionella pneumophila*, a nucleotide region from position 77 to 287 of the cop gene (SEQ ID NO: 71) of *Moraxella catarrhalis*, a nucleotide region from position 4207 to 4596 of the P1 gene (SEQ ID NO: 72) of *Mycoplasma pneumoniae*, a nucleotide region from position 252 to 778 of the ETA gene (SEQ ID NO: 73) of *Pseudomonas aeruginosa*, and a nucleotide region from position 137 to 342 of the lytA gene (SEQ ID NO: 74) of *Streptococcus pneumoniae*.

In the present application, the position of the target sequence refers to a position based on the position from the 5' end of a sense strand. Further, the binding position of the primer and probe also refer to a position based on the position from the 5' end of a sense strand.

The oligonucleotide primer set can comprise an oligonucleotide set selected from the group consisting of: an oligonucleotide set comprising an oligonucleotide consisting of the nucleotide sequence as set forth in SEQ ID NO: 1 and an oligonucleotide consisting of the nucleotide sequence as set forth in SEQ ID NO: 2, wherein the oligonucleotide set specifically amplifies a nucleotide region from position 126 to 227 of the adeB gene of *Acinetobacter baumannii* (SEQ ID NO: 63) and the oligonucleotides hybridize specifically to the adeB gene of *Acinetobacter baumannii* (SEQ ID NO:63); an oligonucleotide set comprising an oligonucleotide consisting of the nucleotide sequence as set forth in SEQ ID NO: 3 and an oligonucleotide consisting of the nucleotide sequence as set forth in SEQ ID NO: 4, wherein the oligonucleotide primer set specifically amplifies a nucleotide region from position 64 to 428 of the Tcf gene of *Bordetella pertussis* (SEQ ID NO: 64) and the oligonucleotides hybridize specifically to the Tcf gene of *Bordetella pertussis*; an oligonucleotide set comprising an oligonucleotide consisting of the nucleotide sequence as set forth in SEQ ID NO: 5 and an oligonucleotide consisting of the nucleotide sequence as set forth in SEQ ID NO: 6, wherein the oligonucleotide primer set specifically amplifies a nucleotide region from position 413 to 622 of the Omp gene of *Chlamydophila pneumoniae* (SEQ ID NO: 65) and the oligonucleotides hybridize specifically to the Omp gene of *Chlamydophila pneumoniae*; an oligonucleotide set comprising an oligonucleotide consisting of the nucleotide sequence as set forth in SEQ ID NO: 7 and an oligonucleotide consisting of the nucleotide sequence as set forth in SEQ ID NO: 8, wherein the oligonucleotide primer set specifically amplifies a nucleotide region from position 1267 to 1689 of the tsx gene of *Enterobacter aerogenes* (SEQ ID NO: 66) and the oligonucleotides hybridize specifically to the tsx gene of *Enterobacter aerogenes*; an oligonucleotide set comprising an oligonucleotide consisting of the nucleotide sequence as set forth in SEQ ID NO: 9 and an oligonucleotide consisting of the nucleotide sequence as set forth in SEQ ID NO: 10, wherein the oligonucleotide primer set specifically amplifies a nucleotide region from position 797 to 912 of the rpoS gene of *Enterobacter cloacae* (SEQ ID NO: 67) and the oligonucleotides hybridize specifically to the rpoS gene of *Enterobacter cloacae*; an oligonucleotide set comprising an oligonucleotide consisting of the nucleotide sequence as set forth in SEQ ID NO: 11 and an oligonucleotide consisting of the nucleotide sequence as set forth in SEQ ID NO: 12, wherein the oligonucleotide primer set specifically amplifies a nucleotide region from position 855 to 976 of the uspA gene of *Escherichia coli* (SEQ ID NO: 68) and the oligonucleotides hybridize specifically to the uspA gene of *Escherichia coli*; an oligonucleotide set comprising an oligonucleotide consisting of the nucleotide sequence as set forth in SEQ ID NO: 13 and an oligonucleotide consisting of the nucleotide sequence as set forth in SEQ ID NO: 14, wherein the oligonucleotide primer set specifically amplifies a nucleotide region from position 89 to 419 of the Wab gene of *Klebsiella pneumoniae* (SEQ ID NO: 69) and the oligonucleotides hybridize specifically to the Wab gene of *Klebsiella pneumoniae*; an oligonucleotide set comprising an oligonucleotide consisting of the nucleotide sequence as set forth in SEQ ID NO: 15 and an oligonucleotide consisting of the nucleotide sequence as set forth in SEQ ID NO: 16, wherein the oligonucleotide primer set specifically amplifies a nucleotide region from position 105 to 469 of the Mip gene of *Legionella pneumophila* (SEQ ID NO: 70) and the oligonucleotides hybridize specifically to the Mip gene of *Legionella pneumophila*; an oligonucleotide set comprising an oligonucleotide consisting of the nucleotide sequence as set forth in SEQ ID NO: 17 and an oligonucleotide consisting of the nucleotide sequence as set forth in SEQ ID NO: 18, wherein the oligonucleotide primer set specifically amplifies a nucleotide region from position 77 to 287 of the cop gene of *Moraxella catarrhalis* (SEQ ID NO: 71) and the oligonucleotides hybridize specifically to the cop gene of *Moraxella catarrhalis*; an oligonucleotide set comprising an oligonucleotide consisting of the nucleotide sequence as set forth in SEQ ID NO: 19 and an oligonucleotide consisting of the nucleotide sequence as set forth in SEQ ID NO: 20, wherein the oligonucleotide primer set specifically amplifies a nucleotide region from position 4207 to 4596 of the P1 gene of *Mycoplasma pneumoniae* (SEQ ID NO: 72) and the oligonucleotides hybridize specifically to the P1 gene of *Mycoplasma pneumoniae*; an oligonucleotide set comprising an oligonucleotide consisting of the nucleotide sequence as set forth in SEQ ID NO: 21 and an oligonucleotide consisting of the nucleotide sequence as set forth in SEQ ID NO: 22, wherein the oligonucleotide primer set specifically amplifies a nucleotide region from position 252 to 778 of the ETA gene of *Pseudomonas aeruginosa* (SEQ ID NO: 73) and the oligonucleotides hybridize specifically to the ETA gene of *Pseudomonas aeruginosa*; and an oligonucleotide set comprising an oligonucleotide consisting of the nucleotide sequence as set forth in SEQ ID NO: 23 and an oligonucleotide consisting of the nucleotide sequence as set forth in SEQ ID NO: 24, wherein the oligonucleotide primer set specifically amplifies a nucleotide region from position 137 to 342 of the lytA gene of *Streptococcus pneumoniae* (SEQ ID NO: 74) and the oligonucleotides hybridize specifically to lytA gene of *Streptococcus pneumoniae*.

In an embodiment, the oligonucleotide primer set comprises an oligonucleotide consisting of the nucleotide sequence as set forth in SEQ ID NO: 1 and an oligonucleotide consisting of the nucleotide sequence as set forth in SEQ ID NO: 2, wherein the oligonucleotide set specifically amplifies a nucleotide region from position 126 to 227 of the adeB gene of *Acinetobacter baumannii* (SEQ ID NO: 63) and the oligonucleotides hybridize specifically to the adeB gene of *Acinetobacter baumannii* (SEQ ID NO: 63); an oligonucleotide set comprising an oligonucleotide consisting of the nucleotide sequence as set forth in SEQ ID NO: 3 and an oligonucleotide consisting of the nucleotide sequence as set forth in SEQ ID NO: 4, wherein the oligonucleotide primer set specifically amplifies a nucleotide region from position 64 to 428 of the Tcf gene of *Bordetella pertussis* (SEQ ID NO: 64) and the oligonucleotides hybridize specifically to the Tcf gene of *Bordetella pertussis*; an oligonucleotide set comprising an oligonucleotide consisting of the nucleotide sequence as set forth in SEQ ID NO: 7 and an oligonucleotide consisting of the nucleotide sequence as set forth in SEQ ID NO: 8, wherein the oligonucleotide primer set specifically amplifies a nucleotide region from position 1267 to 1689 of the tsx gene of *Enterobacter aerogenes* (SEQ ID NO: 66) and the oligonucleotides hybridize specifically to the tsx gene of *Enterobacter aerogenes*; an oligonucleotide set comprising an oligonucleotide consisting of the nucleotide sequence as set forth in SEQ ID NO: 9 and an oligonucleotide consisting of the nucleotide sequence as set forth in SEQ ID NO: 10, wherein the oligonucleotide primer set specifically amplifies a nucleotide region from position 797 to 912 of the rpoS gene of *Enterobacter cloacae* (SEQ ID NO: 67) and the oligonucleotides hybridize specifically to the rpoS gene of *Enterobacter cloacae*.; an oligonucleotide set comprising an oligonucleotide consisting of the nucleotide sequence as set forth in SEQ ID NO: 11 and an oligonucleotide consisting of the nucleotide sequence as set forth in SEQ ID NO: 12, wherein the oligonucleotide primer set specifically amplifies a nucleotide region from position 855 to 976 of the uspA gene of *Escherichia coli* (SEQ ID NO: 68) and the oligonucleotides hybridize specifically to the uspA gene of *Escherichia coli*; an oligonucleotide set comprising an oligonucleotide consisting of the nucleotide sequence as set forth in SEQ ID NO: 13 and an oligonucleotide consisting of the nucleotide sequence as set forth in SEQ ID NO: 14, wherein the oligonucleotide primer set specifically amplifies a nucleotide region from position 89 to 419 of the Wab gene of *Klebsiella pneumoniae* (SEQ ID NO: 69) and the oligonucleotides hybridize specifically to the Wab gene of *Klebsiella pneumoniae*; an oligonucleotide set comprising an oligonucleotide consisting of the nucleotide sequence as set forth in SEQ ID NO: 15 and an oligonucleotide consisting of the nucleotide sequence as set forth in SEQ ID NO: 16, wherein the oligonucleotide primer set specifically amplifies a nucleotide region from position 105 to 469 of the Mip gene of *Legionella pneumophila* (SEQ ID NO: 70) and the oligonucleotides hybridize specifically to the Mip gene of *Legionella pneumophila*; an oligonucleotide set comprising an oligonucleotide consisting of the nucleotide sequence as set forth in SEQ ID NO: 17 and an oligonucleotide consisting of the nucleotide sequence as set forth in SEQ ID NO: 18, wherein the oligonucleotide primer set specifically amplifies a nucleotide region from position 77 to 287 of the cop gene of *Moraxella catarrhalis* (SEQ ID NO: 71) and the oligonucleotides hybridize specifically to the cop gene of *Moraxella catarrhalis*; an oligonucleotide set comprising an oligonucleotide consisting of the nucleotide sequence as set forth in SEQ ID NO: 21 and an oligonucleotide consisting of the nucleotide sequence as set forth in SEQ ID NO: 22, wherein the oligonucleotide primer set specifically amplifies a nucleotide region from position 252 to 778 of the ETA gene of *Pseudomonas aeruginosa* (SEQ ID NO: 73) and the oligonucleotides hybridize specifically to the ETA gene of *Pseudomonas aeruginosa* . . . ; and an oligonucleotide set comprising an oligonucleotide consisting of the nucleotide sequence as set forth in SEQ ID NO: 23 and an oligonucleotide consisting of the nucleotide sequence as set forth in SEQ ID NO: 24, wherein the oligonucleotide primer set specifically amplifies a nucleotide region from position 137 to 342 of the lytA gene of *Streptococcus pneumoniae* (SEQ ID NO: 74) and the oligonucleotides hybridize specifically to lytA gene of *Streptococcus pneumoniae*. In some embodiments, the oligonucleotide primer set further comprises an oligonucleotide set comprising an oligonucleotide consisting of the nucleotide sequence as set forth in SEQ ID NO: 5 and an oligonucleotide consisting of the nucleotide sequence as set forth in SEQ ID NO: 6, wherein the oligonucleotide primer set specifically amplifies a nucleotide region from position 413 to 622 of the Omp gene of *Chlamydophila pneumoniae* (SEQ ID NO: 65) and the oligonucleotides hybridize specifically to the Omp gene of *Chlamydophila pneumoniae*; and an oligonucleotide set comprising an oligonucleotide consisting of the nucleotide sequence as set forth in SEQ ID NO: 19 and an oligonucleotide consisting of the nucleotide sequence as set forth in SEQ ID NO: 20, wherein the oligonucleotide primer set specifically amplifies a nucleotide region from position 4207 to 4596 of the P1 gene of *Mycoplasma pneumoniae* (SEQ ID NO: 72) and the oligonucleotides hybridize specifically to the P1 gene of *Mycoplasma pneumoniae*. The primer set of the present invention was designed from predetermined regions of virulence factor genes encoding virulence factors specifically expressed in twelve respiratory disease-causing bacterial species. Genes encoding virulence factors specifically expressed in the twelve respiratory disease-causing bacterial species include the adeB gene of *Acinetobacter baumannii*, the Tcf gene of *Bordetella pertussis*, the Omp gene of *Chlamydophila pneumoniae*, the tsx gene of *Enterobacter aerogenes*, the rpoS gene of *Enterobacter cloacae*, the uspA gene of *Escherichia coli*, the Wab gene of *Klebsiella pneumoniae*, the Mip gene of *Legionella pneumophila*, the cop gene of *Moraxella catarrhalis*, the P1 gene of *Mycoplasma pneumoniae*, the ETA gene of *Pseudomonas aeruginosa*, and the lytA gene of *Streptococcus pneumoniae*.

When performing PCR using the primer set of the present invention, a target sequence region sought to be amplified may be selected from the nucleotide region from position 126 to 227 of the adeB gene of *Acinetobacter baumannii*, the nucleotide region from position 64 to 428 of the Tcf gene of *Bordetella pertussis*, the nucleotide region from position 413 to 622 of the Omp gene of *Chlamydophila pneumoniae*, the nucleotide region from position 1267 to 1689 of the tsx gene of *Enterobacter aerogenes*, the nucleotide region from position 797 to 912 of the rpoS gene of *Enterobacter cloacae*, the nucleotide region from position 855 to 976 of the uspA gene of *Escherichia coli*, the nucleotide region from position 89 to 419 of the Wab gene of *Klebsiella pneumoniae*, the nucleotide region from position 105 to 469 of the Mip gene of *Legionella pneumophila*, the nucleotide region from position 77 to 287 of the cop gene of *Moraxella catarrhalis*, the nucleotide region from position 4207 to 4596 of the P1 gene of *Mycoplasma pneumoniae*, the nucleotide region from position 252 to 778 of the ETA gene of *Pseudomonas aeruginosa*, and the nucleotide region from position 137 to 342 of the lytA gene of *Streptococcus pneumoniae*.

The primer set of the present invention was designed from target sequences of genes encoding virulence factors specifically expressed in the twelve respiratory disease-causing bacterial species as described in Example 1. A primer set according to an exemplary embodiment of the present invention and target sequence regions amplified using the primer set are presented in Table 1 below.

TABLE 1 a primer set according to an exemplary embodiment of the present invention and target sequence regions amplified using the primer set

| Bacterial species and virulence factor gene | Primer (SEQ ID NO) | Amplification region |
| --- | --- | --- |
| adeB gene of *Acinetobacter baumannii* (SEQ ID NO: 63) | 1<br>2 | Nucleotide region from position 126 to 227 |
| Tcf gene of *Bordetella pertussis* (SEQ ID NO: 64) | 3<br>4 | Nucleotide region from position 64 to 428 |
| Omp gene of *Chlamydophila pneumoniae* (SEQ ID NO: 65) | 5<br>6 | Nucleotide region from position 413 to 622 |
| tsx gene of *Enterobacter aerogenes* (SEQ ID NO: 66) | 7<br>8 | Nucleotide region from position 1267 to 1689 |
| rpoS gene of *Enterobacter cloacae* (SEQ ID NO: 67) | 9<br>10 | Nucleotide region from position 797 to 912 |
| uspA gene of *Escherichia coli* (SEQ ID NO: 68) | 11<br>12 | Nucleotide region from position 855 to 976 |
| Wab gene of *Klebsiella pneumoniae* (SEQ ID NO: 69) | 13<br>14 | Nucleotide region from position 89 to 419 |
| Mip gene of *Legionella pneumophila* (SEQ ID NO: 70) | 15<br>16 | Nucleotide region from position 105 to 469 |
| cop gene of *Moraxella catarrhalis* (SEQ ID NO: 71) | 17<br>18 | Nucleotide region from position 77 to 287 |
| P1 gene of *Mycoplasma pneumoniae* (SEQ ID NO: 72) | 19<br>20 | Nucleotide region from position 4207 to 4596 |
| ETA gene of *Pseudomonas aeruginosa* (SEQ ID NO: 73) | 21<br>22 | Nucleotide region from position 252 to 778 |
| lytA gene of *Streptococcus pneumoniae* (SEQ ID NO: 74) | 23<br>24 | Nucleotide region from position 137 to 342 |

The present invention also provides an oligonucleotide probe set capable of hybridizing with at least one target sequence selected from the group consisting of a nucleotide region from position 126 to 227 of the adeB gene of *Acinetobacter baumannii*, a nucleotide region from position 64 to 428 of the Tcf gene of *Bordetella pertussis*, a nucleotide region from position 413 to 622 of the Omp gene of *Chlamydophila pneumoniae*, a nucleotide region from position 1267 to 1689 of the tsx gene of *Enterobacter aerogenes*, a nucleotide region from position 797 to 912 of the rpoS gene of *Enterobacter cloacae*, a nucleotide region from position 855 to 976 of the uspA gene of *Escherichia coli*, a nucleotide region from position 89 to 419 of the Wab gene of *Klebsiella pneumoniae*, a nucleotide region from position 105 to 469 of the Mip gene of *Legionella pneumophila*, a nucleotide region from position 77 to 287 of the cop gene of *Moraxella catarrhalis*, a nucleotide region from position 4207 to 4596 of the P1 gene of *Mycoplasma pneumoniae*, a nucleotide region from position 252 to 778 of the ETA gene of *Pseudomonas aeruginosa*, and a nucleotide region from position 137 to 342 of the lytA gene of *Streptococcus pneumoniae*, the oligonucleotide probe set including at least one oligonucleotide probe selected from the group consisting of: an oligonucleotide probe capable of hybridizing with the nucleotide region from position 126 to 227 of the adeB gene of *Acinetobacter baumannii*, including at least one oligonucleotide selected from the group consisting of oligonucleotides which include at least 10 contiguous nucleotides present in at least one nucleotide sequence selected from the group consisting of nucleotide sequences as set forth in SEQ ID NOS: 25-27 and complementary oligonucleotides thereof; an oligonucleotide probe capable of hybridizing with the nucleotide region from position 64 to 428 of the Tcf gene of *Bordetella pertussis*, including at least one oligonucleotide selected from the group consisting of oligonucleotides which include at least 10 contiguous nucleotides present in at least one nucleotide sequence selected from the group consisting of nucleotide sequences as set forth in SEQ ID NOS: 28-31 and complementary oligonucleotides thereof; an oligonucleotide probe capable of hybridizing with the nucleotide region from position 413 to 622 of the Omp gene of *Chlamydophila pneumoniae*, including at least one oligonucleotide selected from the group consisting of oligonucleotides which include at least 10 contiguous nucleotides present in at least one nucleotide sequence selected from the group consisting of nucleotide sequences as set forth in SEQ ID NOS: 32-33 and complementary oligonucleotides thereof; an oligonucleotide probe capable of hybridizing with the nucleotide region from position 1267 to 1689 of the tsx gene of *Enterobacter aerogenes*, including at least one oligonucleotide selected from the group consisting of oligonucleotides which include at least 10 contiguous nucleotides present in at least one nucleotide sequence selected from the group consisting of nucleotide sequences as set forth in SEQ ID NOS: 34-35 and complementary oligonucleotides thereof; an oligonucleotide probe capable of hybridizing with the nucleotide region from position 797 to 912 of the rpoS gene of *Enterobacter cloacae*, including at least one oligonucleotide selected from the group consisting of oligonucleotides which include at least 10 contiguous nucleotides present in at least one nucleotide sequence selected from the group consisting of nucleotide sequences as set forth in SEQ ID NOS: 36-39 and complementary oligonucleotides thereof; an oligonucleotide probe capable of hybridizing with the nucleotide region from position 855 to 976 of the uspA gene of *Escherichia coli*, including at least one oligonucleotide selected from the group consisting of oligonucleotides which include at least 10 contiguous nucleotides present in at least one nucleotide sequence selected from the group consisting of nucleotide sequences as set forth in SEQ ID NOS: 40-44 and complementary oligonucleotides thereof; an oligonucleotide probe capable of hybridizing with the nucleotide region from position 89 to 419 of the Wab gene of *Klebsiella pneumoniae*, including at least one oligonucleotide selected from the group consisting of oligonucleotides which include at least 10 contiguous nucleotides present in at least one nucleotide sequence selected from the group consisting of nucleotide sequences as set forth in SEQ ID NOS: 45-46 and complementary oligonucleotides thereof; an oligonucleotide probe capable of hybridizing with the nucleotide region from position 105 to 469 of the Mip gene of *Legionella pneumophila*, including at least one oligonucleotide selected from the group consisting of oligonucleotides which include at least 10 contiguous nucleotides present in at least one nucleotide sequence selected from the group consisting of nucleotide sequences as set forth in SEQ ID NOS: 47-48 and complementary oligonucleotides thereof; an oligonucleotide probe capable of hybridizing with the nucleotide region from position 77 to 287 of the cop gene of *Moraxella catarrhalis*, including at least one oligonucleotide selected from the group consisting of oligonucleotides which include at least 10 contiguous nucleotides present in a nucleotide sequence as set forth in SEQ ID NO: 49 and complementary oligonucleotides thereof; an oligonucleotide probe capable of hybridizing with the nucleotide region from position 4207 to 4596 of the P1 gene of *Mycoplasma pneumoniae*, including at least one oligonucleotide selected from the group consisting of oligonucleotides which include at least 10 contiguous nucleotides present in at least one nucleotide sequence selected from the group consisting of nucleotide sequences as set forth in SEQ ID NOS: 50-51 and complementary oligonucleotides thereof; an oligonucleotide probe capable of hybridizing with the nucleotide region from position 252 to 778 of the ETA gene of *Pseudomonas aeruginosa*, including at least one oligonucleotide selected from the group consisting of oligonucleotides which include at least 10 contiguous nucleotides present in at least one nucleotide sequence selected from the group consisting of nucleotide sequences as set forth in SEQ ID NOS: 52-55 and complementary oligonucleotides thereof; and an oligonucleotide probe capable of hybridizing with the nucleotide region from position 137 to 342 of the lytA gene of *Streptococcus pneumoniae*, including at least one oligonucleotide selected from the group consisting of oligonucleotides which include at least 10 contiguous nucleotides present in at least one nucleotide sequence selected from the group consisting of nucleotide sequences as set forth in SEQ ID NOS: 56-58 and complementary oligonucleotides thereof.

In an embodiment, the oligonucleotide probe set comprises: an oligonucleotide capable of specifically hybridizing with a nucleotide region from position 126 to 227 of an adeB gene of *Acinetobacter baumannii* (SEQ ID NO:63) consisting of at least 10 contiguous nucleotides present in a nucleotide sequence selected from the group consisting of nucleotide sequences as set forth in SEQ ID NOS: 25-27 and complements thereof; an oligonucleotide capable of specifically hybridizing with a nucleotide region from position 64 to 428 of a Tcf gene of *Bordetella pertussis* (SEQ ID NO:64), consisting of at least 10 contiguous nucleotides present in a nucleotide sequence selected from the group consisting of nucleotide sequences as set forth in SEQ ID NOS: 28-31 and complements thereof; an oligonucleotide capable of specifically hybridizing with a nucleotide region from position 413 to 622 of an Omp gene of *Chlamydophila pneumoniae* (SEQ ID NO:65), consisting of at least 10 contiguous nucleotides present in a nucleotide sequence selected from the group consisting of nucleotide sequences as set forth in SEQ ID NOS: 32-33 and complements thereof; an oligonucleotide capable of specifically hybridizing with a nucleotide region from position 1267 to 1689 of a tsx gene of *Enterobacter aerogenes* (SEQ ID NO:66), consisting of at least 10 contiguous nucleotides present in a nucleotide sequence selected from the group consisting of nucleotide sequences as set forth in SEQ ID NOS: 34-35 and complements thereof; an oligonucleotide capable of specifically hybridizing with a nucleotide region from position 797 to 912 of a rpoS gene of *Enterobacter cloacae* (SEQ ID NO:67), consisting of at least 10 contiguous nucleotides present in a nucleotide sequence selected from the group consisting of nucleotide sequences as set forth in SEQ ID NOS: 36-39 and complements thereof; an oligonucleotide capable of specifically hybridizing with a nucleotide region from position 855 to 976 of a uspA gene of *Escherichia coli* (SEQ ID NO:68), consisting of at least 10 contiguous nucleotides present in a nucleotide sequence selected from the group consisting of nucleotide sequences as set forth in SEQ ID NOS: 40-44 and complements thereof; an oligonucleotide capable of specifically hybridizing with a nucleotide region from position 89 to 419 of a Wab gene of *Klebsiella pneumoniae* (SEQ ID NO:69), consisting of at least 10 contiguous nucleotides present in a nucleotide sequence selected from the group consisting of nucleotide sequences as set forth in SEQ ID NOS: 45-46 and complements thereof; an oligonucleotide capable of specifically hybridizing with a nucleotide region from position 105 to 469 of a Mip gene of *Legionella pneumophila* (SEQ ID NO:70), consisting of at least 10 contiguous nucleotides present in a nucleotide sequence selected from the group consisting of nucleotide sequences as set forth in SEQ ID NOS: 47-48 and complements thereof; an oligonucleotide capable of specifically hybridizing with a nucleotide region from position 77 to 287 of a cop gene of *Moraxella catarrhalis* (SEQ ID NO:71), consisting of at least 10 contiguous nucleotides present in a nucleotide sequence as set forth in SEQ ID NO: 49 and complements thereof; an oligonucleotide capable of specifically hybridizing with a nucleotide region from position 4207 to 4596 of a P1 gene of *Mycoplasma pneumoniae* (SEQ ID NO:72), consisting of at least 10 contiguous nucleotides present in a nucleotide sequence selected from the group consisting of nucleotide sequences as set forth in SEQ ID NOS: 50-51 and complements thereof; an oligonucleotide capable of hybridizing with a nucleotide region from position 252 to 778 of an ETA gene of *Pseudomonas aeruginosa* (SEQ ID NO:73), consisting of at least 10 contiguous nucleotides present in a nucleotide sequence selected from the group consisting of nucleotide sequences as set forth in SEQ ID NOS: 52-55 and complements thereof; or an oligonucleotide capable of specifically hybridizing with a nucleotide region from position 137 to 342 of a lytA gene of *Streptococcus pneumoniae* (SEQ ID NO:74), consisting of at least 10 contiguous nucleotides present in a nucleotide sequence selected from the group consisting of nucleotide sequences as set forth in SEQ ID NOS: 56-58 and complements thereof.

The oligonucleotide probe set can comprise an oligonucleotide capable of specifically hybridizing with a nucleotide region from position 126 to 227 of an adeB gene of *Acinetobacter baumannii* (SEQ ID NO:63) consisting of at least 10 contiguous nucleotides present in a nucleotide sequence selected from the group consisting of nucleotide sequences as set forth in SEQ ID NOS: 25-27 and complements thereof; an oligonucleotide capable of specifically hybridizing with a nucleotide region from position 64 to 428 of a Tcf gene of *Bordetella pertussis* (SEQ ID NO:64), consisting of at least 10 contiguous nucleotides present in a nucleotide sequence selected from the group consisting of nucleotide sequences as set forth in SEQ ID NOS: 28-31 and complements thereof; an oligonucleotide capable of specifically hybridizing with a nucleotide region from position 1267 to 1689 of a tsx gene of *Enterobacter aerogenes* (SEQ ID NO:66), consisting of at least 10 contiguous nucleotides present in a nucleotide sequence selected from the group consisting of nucleotide sequences as set forth in SEQ ID NOS: 34-35 and complements thereof; an oligonucleotide capable of specifically hybridizing with a nucleotide region from position 797 to 912 of a rpoS gene of *Enterobacter cloacae* (SEQ ID NO:67) consisting of at least 10 contiguous nucleotides present in a nucleotide sequence selected from the group consisting of nucleotide sequences as set forth in SEQ ID NOS: 36-39 and complements thereof; an oligonucleotide capable of specifically hybridizing with a nucleotide region from position 855 to 976 of a uspA gene of *Escherichia coli* (SEQ ID NO:68), consisting of at least 10 contiguous nucleotides present in a nucleotide sequence selected from the group consisting of nucleotide sequences as set forth in SEQ ID NOS: 40-44 and complements thereof; an oligonucleotide capable of specifically hybridizing with a nucleotide region from position 89 to 419 of a Wab gene of *Klebsiella pneumoniae* (SEQ ID NO:69), consisting of at least 10 contiguous nucleotides present in a nucleotide sequence selected from the group consisting of nucleotide sequences as set forth in SEQ ID NOS: 45-46 and complements thereof; an oligonucleotide capable of specifically hybridizing with a nucleotide region from position 105 to 469 of a Mip gene of *Legionella pneumophila* (SEQ ID NO:70), consisting of at least 10 contiguous nucleotides present in a nucleotide sequence selected from the group consisting of nucleotide sequences as set forth in SEQ ID NOS: 47-48 and complements thereof; an oligonucleotide capable of specifically hybridizing with a nucleotide region from position 77 to 287 of a cop gene of *Moraxella catarrhalis* (SEQ ID NO:71), consisting of at least 10 contiguous nucleotides present in a nucleotide sequence as set forth in SEQ ID NO: 49 and complements thereof; an oligonucleotide capable of hybridizing with a nucleotide region from position 252 to 778 of an ETA gene of *Pseudomonas aeruginosa* (SEQ ID NO:73), consisting of at least 10 contiguous nucleotides present in a nucleotide sequence selected from the group consisting of nucleotide sequences as set forth in SEQ ID NOS: 52-55 and complements thereof; and an oligonucleotide capable of specifically hybridizing with a nucleotide region from position 137 to 342 of a lytA gene of *Streptococcus pneumoniae* (SEQ ID NO:74), consisting of at least 10 contiguous nucleotides present in a nucleotide sequence selected from the group consisting of nucleotide sequences as set forth in SEQ ID NOS: 56-58 and complements thereof. In some embodiments the oligonucleotide probe set further comprises an oligonucleotide capable of specifically hybridizing with a nucleotide region from position 413 to 622 of an Omp gene of *Chlamydophila pneumoniae* (SEQ ID NO:65), consisting of at least 10 contiguous nucleotides present in a nucleotide sequence selected from the group consisting of nucleotide sequences as set forth in SEQ ID NOS: 32-33 and complements thereof; and an oligonucleotide capable of specifically hybridizing with a nucleotide region from position 4207 to 4596 of a P1 gene of *Mycoplasma pneumoniae* (SEQ ID NO:72), consisting of at least 10 contiguous nucleotides present in a nucleotide sequence selected from the group consisting of nucleotide sequences as set forth in SEQ ID NOS: 50-51 and complements thereof.

The probe set of the present invention specifically binds with target regions of virulence factor genes specifically expressed in one or more of the twelve bacterial species or to PCR products amplified from the target regions by PCR using the primer set of the present invention. Thus, the probe set of the present invention can discriminate the twelve bacterial species. The probe set of the present invention was designed by aligning sequences of virulence factor genes specific to the twelve bacterial species and selecting for each bacterial species a sequence specifically present in the bacterial species in the target region for specific amplification. Each probe, specific to a specific bacterial species of the present invention, was selected by comparing the sequences of the virulence factor genus specific to the twelve bacterial species and selecting a probe binding to the virulence factor gene of the specific bacterial species and not to the other virulence factor genes of the other 11 bacterial species.

The process of designing primers of the present invention is more specifically described as follows: firstly, target bacterial species and virulence factor genes specific to the bacterial species were selected by searching a respiratory disease-associated database (VFDB: http://zdsys.chgb.org.cnNFs/main.htm) and related documents (Microbiol. Immunol., 48(6), 441-448, 2004; Infection and Immunity Vol. 72, No. 5, May 2004, p. 2457-2461; J. Bact. Vol. 185, No. 5, March, 2003, p. 1608-1615; J. Bact. Vol. 185, No. 24, December, 2003, p. 7213-7221; J. Clinical Microbiol., Vol. 41, No. 7, July 2003, p. 3327-3330; Infection and Immunity Vol. 71, No. 8, August 2003, p. 4389-4397; Clinical Microbiol. Reviews, January 2002, p. 125-144; Infection and Immunity Vol. 69, No. 9, September 2001, p. 5612-5618; J. Biol. Chem. Vol. 275, No. 5, January 2000, pp. 3057-3064; J. Clinical Microbiol., Vol. 36, No. 9, September 1998, p. 2548-2553; Infection and Immunity Vol. 57, No. 8, August 1989, p. 2324-2330; J. Clinical. Microbiol., Vol. 43, No. 1, January 2005, p. 30-35; J. Clinical. Microbiol., Vol. 39, No. 4, April 2001, p. 1553-1558). The VFDB was created and maintained by the State Key Laboratory for Molecular Virology and Genetic Engineering, Beijing, China and the National Center of human Genome research, Beijing, China. Twenty six virulence factor genes of fourteen bacterial species were selected through a sequence alignment program using what criteria for the selection, that is the sequence can be obtained from Genbank DB and can be sequenced. These gene sequences were then subjected to sequence similarity searching with all sequences in GenBank stored in NCBI GENBANK using the blastn program to thereby select for each of twelve bacterial species a virulence factor gene, specific to the bacterial species.

Primers specific to each of the twelve virulence factor genes of the twelve bacterial species were designed from the twelve virulence factor genes. In primer design, thermodynamic coefficients for potential primer sequences were determined using parameters from Santalucia et al. [Santalucia J, Proc. Natl. Acad. Sci. USA 95:1460-1465 (1998)]. Variables for primer design were as follows: the number of ambiguous nucleotide: 0, GC content: 30-70%, non-specifically matched base pairs: <4 bp, <10 contiguous base pairs with other gene sequence, primer length: 19-23 bases, not contain repetitive nucleotides, $\Delta G=137078-162324$, $\Delta Tm=10°$ C., amplicon length: 60-400 bp.

The process of selecting primers is as follows: Firstly, unique region for primer design was selected by the criteria, ambiguous nucleotide is 0, that is, no variant allele is present, GC percent is in the range of 30-70%, elite pair was selected when there is no more than 12 bp contiguous sequence identical with sequences in other species. The length of primer is 19-24 bp. Secondly, candidate primer pairs were selected by the criteria, amplicon length is 60-400 bp, a primer pairs which satisfy minimum length of elite pair, 9 bp or less. Thirdly, the candidate primer pairs were ranked by the criteria, in the order from small to large length of the eliter pair length and from lower to higher delta TM. Fourthly, the elected primer pairs were tested, and the elected primer pairs were removed form the candidate when they produce monomer in a PCR at 72° C. or more of polymerization temperature and at 62° C. annealing temperature or when they are searched by using Blastn and the search results show that evalue <0.05 with sequences in other species. As a result, primer sets targeting virulence factor genes specifically found in the twelve bacterial species presented in Table 1 above were designed.

Probes were selected from respective amplified regions of the virulence factor genes using DNASTAR program and are summarized in Table 2 below. Probes were selected from the region between the forward primer and reverse primer in the targe sequence. Firstly, unique region for probe design was selected from the region between the forward primer and reverse primer in the targe sequence, by the following criteria, ambiguous nucleotide is 0, that is, there is no variant allele, GC percent is in the range of 30-70%, elite pair was selected when there is no more than 12 bp contiguous sequence identical with sequences in other species. The length of probe is 20-24 bp. Secondly, probes were selected from the selected unique sequence present in the region between the forward primer and reverse primer.

As used herein, the term "probe" refers to a single-stranded nucleic acid sequence that can be base-paired with a complementary single-stranded target sequence to form a double-stranded molecule (hybrid). Oligonucleotide probes and primers disclosed herein can have a length of 10 to 100 nucleotides, 15 to 85 nucleotides, 17 to 75 nucleotides, 19 to 65 nucleotides, 21 to 50 nucleotides, or 14 to 25 nucleotides.

As used herein, the term "hybridization" refers to the bonding of two complementary strands of nucleic acid to form a double-stranded molecule (hybrid).

As used herein, "stringency" is the term used to describe a temperature and a solvent composition during hybridization and the subsequent processes. Under high stringency conditions, highly homologous nucleic acid hybrids will be formed. That is, hybrids with no sufficient degree of complementarity will not be formed. Accordingly, the stringency of the assay conditions determines the amount of complementarity which must exist between two nucleic acid strands to form a hybrid. Stringency is chosen to maximize the difference in stability between probe-target hybrids and probe-non-target hybrids.

The present invention also provides a microarray comprising a substrate on which is immobilized an oligonucleotide probe set according to an embodiment of the present invention.

As used herein, the term "microarray" refers to a high-density array of two or more groups of polynucleotides immobilized on a substrate. Here, each of the two or more groups of the polynucleotides of the microarray is immobilized on predetermined regions of the substrate. Microarrays are well known in the art. Examples of such microarrays are disclosed in U.S. Pat. No. 5,445,934 and U.S. Pat. No. 5,744,305, the disclosures of which are incorporated herein in their entireties by reference.

The present invention also provides a method of detecting a respiratory disease-causing bacterial species selected from the group consisting of *Acinetobacter baumannii*, *Bordetella pertussis*, *Chlamydophila pneumoniae*, *Enterobacter aerogenes*, *Enterobacter cloacae*, *Escherichia coli*, *Klebsiella pneumoniae*, *Legionella pneumophila*, *Moraxella catarrhalis*, *Mycoplasma pneumoniae*, *Pseudomonas aeruginosa*, and *Streptococcus pneumoniae*. The method comprises contacting a sample with an oligonucleotide probe set according to an embodiment of the present invention so that a target nucleic acid sequence in the sample hybridizes with the oligonucleotide probe set, wherein the target nucleic acid sequence is a nucleic acid sequence from a respiratory disease-causing bacterial species selected from the group consisting of *Acinetobacter baumannii*, *Bordetella pertussis*, *Chlamydophila pneumoniae*, *Enterobacter aerogenes*, *Enterobacter cloacae*, *Escherichia coli*, *Klebsiella pneumoniae*, *Legionella pneumophila*, *Moraxella catarrhalis*, *Mycoplasma pneumoniae*, *Pseudomonas aeruginosa*, and *Streptococcus pneumoniae*; and detecting a degree of hybridization between the oligonucleotide probe set and the target nucleic acid sequence in the sample.

In the method of the present invention, the target nucleic acid sequence in the sample can be a PCR product obtained by PCR using, as primers, a primer set according to an embodiment of the present invention, and, as a template, DNA derived from at least one respiratory disease-causing bacterial species selected from the group consisting of *Acinetobacter baumannii*, *Bordetella pertussis*, *Chlamydophila pneumoniae*, *Enterobacter aerogenes*, *Enterobacter cloacae*, *Escherichia coli*, *Klebsiella pneumoniae*, *Legionella pneumophila*, *Moraxella catarrhalis*, *Mycoplasma pneumoniae*, *Pseudomonas aeruginosa*, and *Streptococcus pneumoniae*.

In the method of present invention, the DNA can be selected from the group consisting of chromosomal DNA, cDNA, and a fragment thereof.

In the method of the present invention, the target nucleic acid sequence can be labeled with a detectable labeling material. For example, the labeling material can be a fluorescent material, a phosphorescent material, or a radioactive material. Preferably, the labeling material can be Cy-5 or Cy-3.

In the method of the present invention, the oligonucleotide probe set can be immobilized on a microarray substrate.

In the method of the present invention, the hybridization between the target nucleic acid sequence and the oligonucleotide probe set can be performed under a high stringency hybridization condition. For example, the high stringency hybridization condition can be in a 0.12M phosphate buffer including equal moles of $Na_2HPO_4$ and $NaH_2PO_4$, 1 mM EDTA, and 0.02% sodium dodecylsulfate at 65° C.

In the method of the present invention, "PCR" refers to a polymerase chain reaction. PCR is a method for amplifying a target nucleic acid from a primer pair specifically binding with the target nucleic acid using a polymerase. PCR is well known in the art. PCR can also be performed using a commercially available kit. PCR can be classified into single PCR for amplification of only a single target sequence in a single PCR reaction and into multiplex PCR for simultaneous amplification of different target sequences in a single PCR reaction. Multiplex PCR is performed using a plurality of primer pairs.

In an embodiment of the method of the present invention, the detection of at least one of the twelve bacterial species can be achieved by labeling a PCR product that is the target nucleic acid with a detectable signal-emitting material; hybridizing the labeled PCR product with the oligonucleotide probe set; and detecting a signal generated from the hybridization product. The detectable signal can be an optical signal or an electrical signal, but the present invention is not limited thereto. An optically active material can be a fluorescent material or a phosphorescent material. The fluorescent material can be fluorescein, Cy-5, or Cy-3. The PCR product can be unlabeled or labeled with a detectable signal-emitting material before or after hybridization. In the case where the PCR product is unlabeled, hybridization between the PCR product and a probe oligonucleotide can be detected by an electrical signal, but the present invention is not limited thereto.

The present invention also provides a kit for detecting a respiratory disease-causing bacterial species selected from the group consisting of *Acinetobacter baumannii*, *Bordetella pertussis*, *Chlamydophila pneumoniae*, *Enterobacter aerogenes*, *Enterobacter cloacae*, *Escherichia coli*, *Klebsiella pneumoniae*, *Legionella pneumophila*, *Moraxella catarrhalis*, *Mycoplasma pneumoniae*, *Pseudomonas aeruginosa*, and *Streptococcus pneumoniae* in a sample, the kit including a primer set according to an embodiment of the present invention and an instruction manual.

In the kit of the present invention, the primer set is as described above. The instruction manual includes a description specifying how to use the primer set as amplification primers for specific amplification of virulence factor genes specific to the twelve bacterial species. The description can further comprise the length of the specific amplification product for the target region of a respiratory disease-causing bacteria. When a product specific to one of the twelve bacterial species is obtained from an amplification reaction (e.g., PCR) using the kit including the primer set, it is determined that the bacterial species is present in the sample. The kit may include an amplification reagent and a detectable labeling material.

The kit of the present invention may further include an oligonucleotide probe set according to an embodiment of the present invention. The probe set can detect a product obtained by an amplification reaction using the primer set as primers.

Hereinafter, the present invention will be described more specifically with reference to the following examples. The following examples are for illustrative purposes only and are not intended to limit the scope of the invention.

EXAMPLES

Example 1

Selection of Primers for Amplifying Target Sequences Specifically Found in Twelve Respiratory Disease-Causing Bacterial Species In Example 1, genes encoding virulence factors specifically expressed in twelve bacterial species were selected, and primer sets capable of amplifying the genes and probes were designed.

(1) Design of Primers

First, target bacterial species and virulence factor genes specific to the bacterial species were selected by searching a respiratory disease-associated database (VFDB: data base of virulence factors for bacterial pathogens) and related documents (Microbiol. Immunol., 48(6), 441-448, 2004; Infection and Immunity Vol. 72, No. 5, May 2004, p. 2457-2461; J. Bact. Vol. 185, No. 5, March, 2003, p. 1608-1615; J. Bact. Vol. 185, No. 24, December, 2003, p. 7213-7221; J. Clinical Microbiol., Vol. 41, No. 7, July 2003, p. 3327-3330; Infection and Immunity Vol. 71, No. 8, August 2003, p. 4389-4397; Clinical Microbiol. Reviews, January 2002, p. 125-144; Infection and Immunity Vol. 69, No. 9, September 2001, p. 5612-5618; J. Biol. Chem. Vol. 275, No. 5, January 2000, pp. 3057-3064; J. Clinical Microbiol., Vol. 36, No. 9, September 1998, p. 2548-2553; Infection and Immunity Vol. 57, No. 8, August 1989, p. 2324-2330; J. Clinical. Microbiol., Vol. 43, No. 1, January 2005, p. 30-35; J. Clinical. Microbiol., Vol. 39, No. 4, April 2001, p. 1553-1558). The VFDB was created and maintained by the State Key Laboratory for Molecular Virology and Genetic Engineering, Beijing, China and the National Center of human Genome research, Beijing, China. Twenty six virulence factor genes of fourteen bacterial species were selected through a sequence alignment program using what criteria for the selection, that is the sequence can be obtained from Genbank DB and can be sequenced. These gene sequences were then subjected to sequence similarity searching with all sequences in GenBank stored in NCBI GENBANK using the blastn program to thereby select for each of twelve bacterial species a virulence factor gene, specific to the bacterial species.

Primers specific to each of the twelve virulence factor genes of the twelve bacterial species were designed from the twelve virulence factor genes. In primer design, thermodynamic coefficients for potential primer sequences were determined using parameters from Santalucia et al. [Santalucia J, Proc. Natl. Acad. Sci. USA 95:1460-1465 (1998)]. Variables for primer design were as follows: the number of ambiguous nucleotide: 0, GC content: 30-70%, non-specifically matched base pairs: <4 bp, <10 contiguous base pairs with other gene sequence, primer length: 19-23 bases, not contain repetitive nucleotides, $\Delta G$=137078-162324, $\Delta Tm$=10° C., amplicon length: 60-400 bp.

The process of selecting primers is as follows: Firstly, unique region for primer design was selected by the criteria, ambiguous nucleotide is 0, that is, there is no variant alles, GC percent is in the range of 30-70%, elite pair was selected when there is no more than 12 bp contiguous sequence identical with sequences in other species. The length of primer is 19-24 bp. Secondly, candidate primer pairs were selected by the criteria, amplicon length is 60-400 bp, a primer pair which satisfy minimum length of elite pair, 9 bp or less. Thirdly, the candidate primer pairs were ranked by the criteria, in the order from small to large length of the eliter pair length and from lower to higher delta TM. Fourthly, the elected primer pairs were tested, and the elected primer pairs were removed form the candidate when they produce monomer in a PCR at 72° C. or more of polymerizaton temperature and at 62° C. annealing temperature or when they are searched by using Blastn and the search results show that e-value <0.05 with sequences in other species.

As a result, primer sets targeting virulence factor genes specifically found in the twelve bacterial species presented in Table 1 above were designed.

(2) Design of Probes

Probes were selected from respective amplified regions of the virulence factor genes using DNASTAR program and are summarized in Table 2 below. Probes were selected from the region between the forward primer and reverse primer in the targe sequence. Firstly, unique region for probe design was selected from the region between the forward primer and reverse primer in the targe sequence, by the following criteria, ambiguous nucleotide is 0, that is, there is no variant allele, GC percent is in the range of 30-70%, elite pair was selected when there is no more than 12 bp contiguous sequence identical with sequences in other species. The length of probe is 20-24 bp. Secondly, probes were selected from the selected unique sequence present in the region between the forward primer and reverse primer.

TABLE 2

| Probe name | Bacterial target gene | SEQ ID NO | Probe binding position in gene |
| --- | --- | --- | --- |
| Aba-adeB-1-probe1 | adeB gene of *Acinetobacter baumannii* | 25 | 169 |
| Aba-adeB-1-probe2 | adeB gene of *Acinetobacter baumannii* | 26 | 198 |
| Aba-adeB-1-probe3 | adeB gene of *Acinetobacter baumannii* | 27 | 200 |
| Bpe-Tcf-S1-probe1 | Tcf gene of *Bordetella pertussis* | 28 | 96 |
| Bpe-Tcf-S1-probe2 | Tcf gene of *Bordetella pertussis* | 29 | 100 |
| Bpe-Tcf-S1-probe3 | Tcf gene of *Bordetella pertussis* | 30 | 136 |
| Bpe-Tcf-S2-probe2 | Tcf gene of *Bordetella pertussis* | 31 | 242 |

TABLE 2-continued

| Probe name | Bacterial target gene | SEQ ID NO | Probe binding position in gene |
|---|---|---|---|
| Cpn-Omp-S1-probe2 | Omp gene of *Chlamydophila pneumoniae* | 32 | 383 |
| Cpn-Omp-S2-probe3 | Omp gene of *Chlamydophila pneumoniae* | 33 | 555 |
| Eae-tsx-probe10 | tsx gene of *Enterobacter aerogenes* | 34 | 1624 |
| Eae-tsx-probe11 | tsx gene of *Enterobacter aerogenes* | 35 | 1641 |
| Ecl-rpoS-02-p2-t | rpoS gene of *Enterobacter cloacae* | 36 | 833 |
| Ecl-rpoS-02-p4-c1 | rpoS gene of *Enterobacter cloacae* | 37 | 871 |
| Ecl-rpoS-02-p4-t | rpoS gene of *Enterobacter cloacae* | 38 | 871 |
| Ecl-rpoS-02-p2-probe1 | rpoS gene of *Enterobacter cloacae* | 39 | 890 |
| Eco-uspA-probe4 | uspA gene of *Escherichia coli* | 40 | 919 |
| Eco-uspA-probe5 | uspA gene of *Escherichia coli* | 41 | 924 |
| Eco-uspA-probe6 | uspA gene of *Escherichia coli* | 42 | 944 |
| Eco-uspA-probe7-1 | uspA gene of *Escherichia coli* | 43 | 919 |
| Eco-uspA-probe7-2 | uspA gene of *Escherichia coli* | 44 | 944 |
| Kpn-Wab-S2-probe2 | Wab gene of *Klebsiella pneumoniae* | 45 | 169 |
| Kpn-Wab-S2-probe3 | Wab gene of *Klebsiella pneumoniae* | 46 | 271 |
| Lpn-Mip-S1-probe1 | Mip gene of *Legionella pneumophila* | 47 | 172 |
| Lpn-Mip-S1-probe2 | Mip gene of *Legionella pneumophila* | 48 | 179 |
| Mca-cop-S1-probe1 | cop gene of *Moraxella catarrhalis* | 49 | 137 |
| Mca-P1-S1-probe2 | P1 gene of *Mycoplasma pneumoniae* | 50 | 4489 |
| Mpn-P1-S1-probe3 | ETA gene of *Pseudomonas aeruginosa* | 51 | 4492 |
| Pae-ETA-probe1 | ETA gene of *Pseudomonas aeruginosa* | 52 | 1433 |
| Pae-ETA-probe2 | ETA gene of *Pseudomonas aeruginosa* | 53 | 1438 |
| Pae-ETA-probe3 | ETA gene of *Pseudomonas aeruginosa* | 54 | 1444 |
| Pae-ETA-probe4 | ETA gene of *Pseudomonas aeruginosa* | 55 | 1446 |
| Spn-Lyt-S2-probe2 | LytA gene of *Streptococcus pneumoniae* | 56 | 169 |
| Spn-Lyt-S3-probe1 | LytA gene of *Streptococcus pneumoniae* | 57 | 166 |
| Spn-Lyt-S3-probe3 | LytA gene of *Streptococcus pneumoniae* | 58 | 191 |

Example 2

Amplification of Virulence Factor Genes Specific to Ten Respiratory Disease-Associated Bacterial Species Using Primer Sets of the Present Invention Virulence factor genes specific to ten respiratory disease-associated bacterial species (excluding *Chlamydophila pneumoniae* and *Mycoplasma pneumoniae*) from among the twelve respiratory disease-associated bacterial species were amplified by single PCR or multiplex PCR using the primer sets designed in Example 1 and presented in Table 1 above. Oligonucleotides as set forth in SEQ ID NOS: 1-4, 7-18, and 21-24 were used as primers. The 5'-ends of all the forward and reverse primers were labeled with Cy-3.

(1) Preparation of Bacterial Cultures

Cultured isolates of the ten bacterial species from the Asian-Pacific Research Foundation for Infectious Diseases (ARFID) were used to obtain genomic DNA to test the specificity and selectivity of the designed primer pairs.

(2) Single PCR

Single PCR was performed using genomic DNAs of each of the ten target bacterial species as templates and each of the individual primer sets (excluding the primer sets specific to *Chlamydophila pneumoniae* and *Mycoplasma pneumoniae*) designed in Example 1 as primers to demonstrate that each bacterial target sequence was specifically amplified by the primer set designed to be specific for that bacterial target sequence.

The bacterial species were divided into six groups, each group including different bacterial species: group 1 (*Acinetobacter calcoaceticus, Acinetobacter lwoffii, Bacillus subtilis, Bordetella avium, Bordetella bronchiseptica,* and *Citrobacter freundii*), group 2 (*Enterococcus faecalis, Enterococcus faecium, Gemella melitensis, Haemophilus aphrophilus, Klebsiella oxytoca, Moraxella nonliquefaciens, Morganella morganii,* and *Proteus mirabilis*), group 3 (*Proteus vulgaris, Pseudomonas fluorescens, Pseudomonas putida, Pseudomonas stutzeri, Salmonella typhi, Salmonella typhimurium, Shigella boydii, Shigella flexneri, Shigella sonnei,* and *Staphylococcus cohnii*), group 4 (*Staphylococcus epidermidis, Staphylococcus gallinarium, Staphylococcus haemolyticus, Staphylococcus hominis, Staphylococcus intermedius, Staphylococcus lentus, Staphylococcus lugdunensis, Staphylococcus xylosus,* CNS, and *Streptococcus agalactiae* (group B)), group 5 (*Streptococcus dysgalactiae, Streptococcus gordonii, Streptococcus intermedius/milleri, Streptococcus mitis, Streptococcus oralis, Streptococcus pyogenes, Streptococcus salivarius* subsp. *thermophilus, Streptococcus sanguinis,* and *Streptococcus suis*), group 6 (*Acinetobacter haemolyticus, Citrobacter freundii, Enterobacter agglomerans, Salmonella bongori, Shigella boydii, Salmonella choleraesuis, Shigella flexneri, Shigella sonnei,* and *Salmonella typhimurium*). Bacterial groups were divided in 6 groups because of too many number of bacterial samples.

The single PCR was performed using 20 µl of a PCR solution of 2 µl of a genomic DNA (extracted using a G-spin genomic DNA extraction kit, iNtRON) in a mixed solution including 1.5 mM of $MgCl_2$, 250 mM of each dNTP, 10 mM tris-HCl (pH 9.0), 1 unit of Taq polymerase, and about 2 pmol of each primer, for 29 minutes and 5 seconds, as follows: 25 cycles of denaturation at 95° C. for 10 seconds, annealing at 60° C. for 10 seconds, and extension at 60° C. for 13 seconds.

As a result, target sequences of the virulence factor genes of the ten respiratory disease-associated bacterial species were amplified by the single PCR (see FIGS. 2 through 6). In FIGS. 2 through 6, S denotes single PCR, M denotes multiplex PCR, and the Arabic numbers denote sample numbers. For the control groups, no PCR products were obtained (data not shown).

(3) Multiplex PCR

Multiplex PCR was also performed using each of the genomic DNA of the ten respiratory disease-associated bacterial species and the mixture of ten primer sets used in the single PCR experiments. The PCR products were identified by hybridization using microarrays on which probes according to the present invention were immobilized and by electrophoresis on an agarose gel. The control bacterial species used in the single PCR were also subjected to multiplex PCR using the 10 primer sets simultaneously.

The PCR mix for the multiplex PCR was made up to a total volume of 50 µl, containing 10.5 µl of distilled water, 7.5 µl of 10× buffer (100 mM Tris-HCl, 500 mM KCl, 15 mM $MgCl_2$, 0.1% Gelatine), 1 µl of 2001 M dNTP (each), 20 µl of 400 nM end-labeled primer (each, Bioneer, Korea), 5 µl of extracted genomic DNA, and 1 µl of Taq polymerase (5 units). Human MODY e9 DNA was used as a positive control. In addition to the ten primer sets, the multiplex PCR solution contained primers specific to the A02 and A07 regions of the 3,300 bp 23S rRNA gene of nine respiratory disease-causing bacterial species, i.e., *Chlamydophila pneumoniae, Haemophilus influenza, Klebsiella pneumoniae, Legionella pneumophila, Moraxella catarrhalis, Mycoplasma pneumoniae, Pseudomonas aeruginosa, Staphylococcus aureus,* and *Streptococcus pneumoniae*. That is, the primers for the A02 and A07 regions were used as universal primers capable of specific amplification of the A02 and A07 regions of 23S rRNA in 7 of the 10 target respiratory-disease causing bacterial species. For primers specific to the A02 region, an oligonucleotide as set forth in SEQ ID NO: 59 was used as a forward primer, and an oligonucleotide as set forth in SEQ ID NO: 60 was used as a reverse primer. For primers specific to the A07 region, an oligonucleotide as set forth in SEQ ID NO: 61 was used as a forward primer, and an oligonucleotide as set forth in SEQ ID NO: 62 was used as a reverse primer. The A02 and A07 regions are respectively a nucleotide region from position 853 to 1353 and a nucleotide region from position 2483 to 2932 in 23S rRNA gene.

The multiplex PCR was performed as follows: initial denaturation at 95° C. for one minute; 25 cycles of denaturation at 95° C. for 5 seconds, annealing at 62° C. for 13 seconds, and extension at 72° C. for 15 seconds; and extension at 72° C. for one minute.

The multiplex PCR products were hybridized with fluorescently labeled oligonucleotide probes specific to the virulence factor genes of the ten bacterial species immobilized on microarrays, and fluorescence emitted from the microarrays were measured (see FIG. B for the immobilized probes).

The microarrrays with the immobilized probe set were manufactured as follows. First, wafers were spin-coated with a solution of GAPTES (γ-aminopropyltriethoxysilane) (20% (v/v)) or GAPDES (γ-aminopropyldiethoxysilane) (20% (v/v)) in ethanol. The spin coating was performed using a spin coater (Model CEE 70, CEE) as follows: initial coating at a rate of 500 rpm/10 sec and main coating at a rate of 2000 rpm/10 sec. After the spin coating was completed, the wafers were placed in a Teflon wafer carrier and cured at 120° C. for 40 minutes. The cured wafers were immersed in water for 10 minutes, ultrasonically washed for 15 minutes, immersed in water for 10 minutes, and dried. The drying was performed using a spin-drier. All the experiments were conducted in a clean room class 1000 where most dust particles had been sufficiently removed.

Oligonucleotide probe sets specific to the virulence factor genes of the ten bacterial species among the twelve bacterial species presented in Table 1 above were immobilized on the amino-activated wafers using a spotting method to thereby obtain microarrays.

The PCR products were applied to the microarrays. The microarrays were incubated at 42 C for one hour so that probe-target hybridization occurred and then washed with a washing buffer. Fluorescence intensity from fluorescently labeled probe was measured using a GenePix Scanner (Molecular Device, U.S.A.).

FIG. 1 presents images showing hybridization results of PCR products obtained using all 10 primer sets specific to the respective virulence factor genes specifically expressed in the ten bacterial species simultaneously as primers and each of the genomic DNA of all the ten bacterial species as templates with the oligonucleotide probes specific to the virulence factor genes of the ten bacterial species.

Referring to FIG. 1, it can be seen that the virulence factor genes specifically found in the ten bacterial species are specifically amplified by multiplex PCR. In FIG. 1, abbreviations for the bacterial species are as follows: Aba: *Acinetobacter baumannii*, Bpe: *Bordetella pertussis*, Eae: *Enterobacter aerogenes*, Ecl: *Enterobacter cloacae*, Eco: *Escherichia coli*, Kpn: *Klebsiella pneumoniae*, Lpn: *Legionella pneumophila*, Mca: *Moraxella catarrhalis*, Pae: *Pseudomonas aeruginosa*, Spn: *Streptococcus pneumoniae*.

As shown in FIG. 1, the ten bacterial species were detected with high sensitivity using the probes designed in Example 1.

An array of the probes spotted on the microararys shown in FIG. 1 is presented in FIG. 1B.

In FIG. 1B, each of the cells in the microarray with rows 1-6 and columns 1-12 includes two spots. The number in a cell represents the sequence identification number of the probe immobilized in the cell on the microarray (see Table 2 above for the probes represented by the sequence identification numbers). The presence of the symbol "−" in a cell indicates that a negative control probe was immobilized int the cell. Empty cells in FIG. 1B represent spots for probes which are not claimed by the present invention, e.g., probes specific to the 23S rRNA gene regions or nonspecific probes. The probes immobilized on the spots corresponding to the empty cells are not associated with the present invention, and thus, a detailed description thereof will be omitted.

FIGS. 2 through 6 show electrophoretic results of PCR products for each target bacterial species obtained by single PCR and multiplex PCR using the ten primer sets. Referring to FIGS. 2 through 6, all ten target sequences were successfully identified by multiplex PCR using the ten primer sets. This result shows that the target sequence specificity of any one of the primer sets as set forth in SEQ ID NOS: 1-4, 7-18, and 21-24 is not affected by that of the other primer sets during the multiplex PCR. In FIGS. 2 through 6, the bands marked by arrows represent the PCR products from the A02 and A07 regions of the 23S rRNA genes amplified by the multiplex PCR using the universal primers. Abbreviations for the bacterial species in FIGS. 2 through 6 are as described above with reference to FIG. 1.

A nucleic acid primer set of the present invention can specifically amplify target sequence(s) present in twelve respiratory disease-causing bacterial species, and thus, can be used for specific and selective detection of at least one of the twelve respiratory disease-causing bacterial species.

A probe or probe set of the present invention is specific for hybridization to a target sequence present in at least one of the twelve respiratory disease-causing bacterial species, and thus, can be used for specific and selective detection of at least one of the twelve respiratory disease-causing bacterial species. The target sequence can be a PCR product amplified using the primer set of the present invention.

A microarray of the present invention can be used for specific and selective detection of at least one of the twelve respiratory disease-causing bacterial species.

According to a detection method of the present invention, twelve respiratory disease-causing bacterial species can be efficiently detected with high specificity and selectivity.

The terminology used herein is for the purpose of describing particular embodiments only and is not intended to be limiting of the invention. The terms "a" and "an" do not denote a limitation of quantity, but rather denote the presence of at least one of the referenced item. The term "or" means "and/or". The terms "comprising", "having", "including", and "containing" are to be construed as open-ended terms (i.e., meaning "including, but not limited to").

Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable.

All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein. Unless defined otherwise, technical and scientific terms used herein have the same meaning as is commonly understood by one of skill in the art to which this invention belongs.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A microarray comprising an oligonucleotide probe set immobilized on a substrate, wherein the oligonucleotide probe set comprises:

an oligonucleotide set comprising an oligonucleotide consisting of SEQ ID NO: 25 or the complement thereof, an oligonucleotide consisting of SEQ ID NO: 26 or the complement thereof, and an oligonucleotide consisting of SEQ ID NO: 27 or the complement thereof, wherein each oligonucleotide in the set is capable of specifically hybridizing with a nucleotide region from position 126 to 227 of an adeB gene of *Acinetobacter baumannii* (SEQ ID NO:63);

an oligonucleotide set comprising an oligonucleotide consisting of SEQ ID NO: 28 or the complement thereof, an oligonucleotide consisting of SEQ ID NO: 29 or the complement thereof, and an oligonucleotide consisting of SEQ ID NO: 31 or the complement thereof, wherein each oligonucleotide in the set is capable of specifically hybridizing with a nucleotide region from position 64 to 428 of a Tcf gene of *Bordetella pertussis* (SEQ ID NO:64);

an oligonucleotide set comprising an oligonucleotide consisting of SEQ ID NO: 34 or the complement thereof, and an oligonucleotide consisting of SEQ ID NO: 35 or the complement thereof, wherein each oligonucleotide in the set is capable of specifically hybridizing with a nucleotide region from position 1267 to 1689 of a tsx gene of *Enterobacter aerogenes* (SEQ ID NO:66);
an oligonucleotide set comprising
an oligonucleotide consisting of SEQ ID NO: 36 or the complement thereof,
an oligonucleotide consisting of SEQ ID NO: 37 or the complement thereof,
an oligonucleotide consisting of SEQ ID NO: 38 or the complement thereof, and
an oligonucleotide consisting of SEQ ID NO: 39 or the complement thereof,
wherein each oligonucleotide in the set is capable of specifically hybridizing with a nucleotide region from position 797 to 912 of a rpoS gene of *Enterobacter cloacae* (SEQ ID NO:67);
an oligonucleotide set comprising
an oligonucleotide consisting of SEQ ID NO: 40 or the complement thereof,
an oligonucleotide consisting of SEQ ID NO: 41 or the complement thereof,
an oligonucleotide consisting of SEQ ID NO: 42 or the complement thereof,
an oligonucleotide consisting of SEQ ID NO: 43 or the complement thereof, and
an oligonucleotide consisting of SEQ ID NO: 44 or the complement thereof, wherein each oligonucleotide in the set is capable of specifically hybridizing with a nucleotide region from position 855 to 976 of a uspA gene of *Escherichia coli* (SEQ ID NO:68);
an oligonucleotide set comprising
an oligonucleotide consisting of SEQ ID NO: 45 or the complement thereof, and
an oligonucleotide consisting of SEQ ID NO: 46 or the complement thereof,
wherein each oligonucleotide in the set is capable of specifically hybridizing with a nucleotide region from position 89 to 419 of a Wab gene of *Klebsiella pneumoniae* (SEQ ID NO:69);
an oligonucleotide set comprising
an oligonucleotide consisting of SEQ ID NO: 47 or the complement thereof, and
an oligonucleotide consisting of SEQ ID NO: 48 or the complement thereof,
wherein each oligonucleotide in the set is capable of specifically hybridizing with a nucleotide region from position 105 to 469 of a Mip gene of *Legionella pneumophila* (SEQ ID NO:70);
an oligonucleotide consisting of SEQ ID NO: 49, wherein the oligonucleotide is capable of specifically hybridizing with a nucleotide region from position 77 to 287 of a cop gene of *Moraxella catarrhalis* (SEQ ID NO:71);
an oligonucleotide set comprising
an oligonucleotide consisting of SEQ ID NO: 52 or the complement thereof,
an oligonucleotide consisting of SEQ ID NO: 53 or the complement thereof,
an oligonucleotide consisting of SEQ ID NO: 54 or the complement thereof, and
an oligonucleotide consisting of SEQ ID NO: 55 or the complement thereof,
wherein each oligonucleotide in the set is capable of hybridizing with a nucleotide region from position 252 to 778 of an ETA gene of *Pseudomonas aeruginosa* (SEQ ID NO:73); and
an oligonucleotide set comprising
an oligonucleotide consisting of SEQ ID NO: 56 or the complement thereof,
an oligonucleotide consisting of SEQ ID NO: 57 or the complement thereof, and
an oligonucleotide consisting of SEQ ID NO: 58 or the complement thereof,
wherein each oligonucleotide in the set is capable of specifically hybridizing with a nucleotide region from position 137 to 342 of a lytA gene of *Streptococcus pneumoniae* (SEQ ID NO:74).

2. The microarray of claim 1, the oligonucleotide probe set further comprising,
an oligonucleotide consisting of SEQ ID NO:32 or the complement thereof, wherein the oligonucleotide is capable of specifically hybridizing with a nucleotide region from position 413 to 622 of an Omp gene of *Chlamydophila pneumoniae* (SEQ ID NO:65);
an oligonucleotide consisting of SEQ ID NO:33 or the complement thereof, wherein the oligonucleotide is capable of specifically hybridizing with a nucleotide region from position 413 to 622 of an Omp gene of *Chlamydophila pneumoniae* (SEQ ID NO:65);
an oligonucleotide consisting of SEQ ID NO:50 or the complement thereof, wherein the oligonucleotide is capable of specifically hybridizing with a nucleotide region from position 4207 to 4596 of a P1 gene of *Mycoplasma pneumoniae* (SEQ ID NO:72); and
an oligonucleotide consisting of SEQ ID NO:51 or the complement thereof, wherein the oligonucleotide is capable of specifically hybridizing with a nucleotide region from position 4207 to 4596 of a P1 gene of *Mycoplasma pneumoniae* (SEQ ID NO:72).

* * * * *